United States Patent [19]

Fürstenwerth

[11] Patent Number: 4,500,715

[45] Date of Patent: Feb. 19, 1985

[54] 2,5-DIAMINO-1,3,4-THIADIAZOLE DERIVATIVES

[75] Inventor: Hauke Fürstenwerth, Cologne, Fed. Rep. of Germany

[73] Assignee: Bayer Aktiengesellschaft, Leverkusen, Fed. Rep. of Germany

[21] Appl. No.: 228,489

[22] Filed: Jan. 26, 1981

Related U.S. Application Data

[62] Division of Ser. No. 20,161, Mar. 13, 1979, Pat. No. 4,268,438.

[30] Foreign Application Priority Data

Mar. 15, 1978 [DE]  Fed. Rep. of Germany ....... 2811258

[51] Int. Cl.³ .................... C07D 285/12; C09B 29/22
[52] U.S. Cl. .................................. 548/140; 544/105; 544/133; 544/145; 544/368; 546/94; 546/95; 546/166; 546/209; 548/139; 548/141; 534/607; 534/710; 534/752; 534/765; 534/768; 534/769; 534/775; 534/778; 534/779; 534/795
[58] Field of Search ......................... 548/141, 139, 140

[56] References Cited

U.S. PATENT DOCUMENTS

| | | | |
|---|---|---|---|
| 2,708,671 | 5/1955 | Towne et al. | 260/158 |
| 3,096,320 | 7/1963 | Lange et al. | 260/158 |
| 3,639,385 | 2/1972 | Weaver | 260/158 |
| 4,006,127 | 2/1977 | Raue et al. | 260/158 |
| 4,036,826 | 7/1979 | Boehmke | 260/158 |
| 4,082,740 | 5/1978 | Mohr et al. | 260/158 |
| 4,281,120 | 7/1981 | Herrling | 544/117 |

FOREIGN PATENT DOCUMENTS

1199411 12/1959  France ................. 260/158

*Primary Examiner*—Glennon H. Hollrah
*Assistant Examiner*—James H. Turnipseed
*Attorney, Agent, or Firm*—Sprung, Horn, Kramer & Woods

[57] ABSTRACT

1,3,4-Thiazole derivatives of the formula

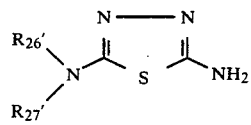

wherein $R_{26}'$ denotes a $C_1$–$C_8$-alkyl radical which is optionally substituted by hydroxyl, halogen, cyano, $C_1$–$C_4$-alkoxy, carboxyl, aminocarbonyl or $C_1$–$C_4$-alkoxycarbonyl, a $C_2$–$C_4$-alkenyl radical, a cyclohexyl radical which is optionally substituted by $C_1$–$C_4$-alkyl, a phenyl, benzyl or phenylethyl radical which is optionally substituted by halogen, $C_1$–$C_4$-alkyl or $C_1$–$C_4$-alkoxy, a $C_1$–$C_2$-alkylcarbonyl, $C_1$–$C_4$-alkoxycarbonyl, mono- or di-$C_1$–$C_4$-alkylaminocarbonyl, aminocarbonyl, mono- or di-$C_1$–$C_4$-alkylaminosulphonyl, 2-thienyl, 2-furyl, 2-tetrahydrofuryl, amino, $C_1$–$C_4$-alkylamino or di-($C_1$–$C_4$-alkyl)-amino radical or a phenylamino or benzylamino radical which is optionally substituted by $C_1$–$C_4$-alkyl or $C_1$–$C_4$-alkoxy and $R_{27}'$ denotes a $C_1$–$C_8$-alkyl radical which is optionally substituted by hydroxyl, halogen, cyano, $C_1$–$C_4$-alkoxy, carboxyl, aminocarbonyl- or $C_1$–$C_4$-alkoxycarbonyl, a $C_2$–$C_4$-alkenyl radical or a benzyl or phenylethyl radical which is substituted by halogen, $C_1$–$C_4$-alkyl or $C_1$–$C_4$-alkoxy, are useful as intermediates for the preparation of pharmaceuticals, agents for protecting plants and dyestuffs.

1 Claim, No Drawings

2,5-DIAMINO-1,3,4-THIADIAZOLE DERIVATIVES

This is a division of application Ser. No. 020,161, filed Mar. 13, 1979, now U.S. Pat. No. 4,268,438.

The present invention relates to cationic dyestuffs which are free from sulphonic acid groups and have the general formula $$\left[ \begin{array}{c} R \\ \diagdown \\ R_1 \end{array} N \underset{S}{\overset{R_2}{\underset{\|}{\bigtriangleup}}} N = N - K \right]^{(+)} \quad An^{(-)} \quad (I)$$

wherein

R denotes hydrogen or an alkyl, alkenyl, acyl, cycloalkyl, aryl, aralkyl, amino, alkylamino, dialkylamino, arylamino, aralkylamino or heterocyclic radical and $R_1$ denotes hydrogen or an alkyl, alkenyl or aralkyl radical, or R and $R_1$ are linked to form a heterocyclic ring with the condition that if R denotes aryl, $R_1$ cannot be hydrogen, $R_2$ denotes an alkyl, alkenyl, alkinyl or aralkyl radical, K denotes a radical of a coupling component and $An^{(-)}$ denotes an anion, and wherein the cyclic and acyclic radicals can contain non-ionic substituents and/or a carboxyl group.

The invention also relates to the preparation of the dyestuffs I and their use for dyeing and printing natural and synthetic materials.

Examples of coupling components are those of the benzene, naphthalene, indole, pyrazole or aliphatic series with a methylene group which is capable of undergoing coupling reactions. Fused benzene derivatives are also to be understood as coupling components of the benzene series, for example radicals of the dihydroindole, tetrahydroquinoline, carbazole, hexahydrocarbazole and julolidine series.

Preferred dyestuffs correspond to the general formula $$\left[ \begin{array}{c} R \\ \diagdown \\ R_1 \end{array} N \underset{S}{\overset{R_2}{\underset{\|}{\bigtriangleup}}} N = N - K_1 \right]^{(+)} \quad An^{(-)} \quad II$$

wherein

R, $R_1$, $R_2$ and $An^-$ have the meaning indicated in formula I and $K_1$ represents a radical of the formula

[structure with $R_4$, $R_5$, $(R_8)_n$]

[structure with $R_6$, $R_7$]

[structure with $(R_{10})_n$, N—$R_9$, $R_8$]

or

[structure with $R_{11}$, N—$R_{12}$, $R_{13}$]

in which $R_3$ denotes hydrogen, alkyl, alkoxy or halogen, $R_4$ and $R_5$ denote hydrogen, alkyl or aralkyl, $R_6$ and $R_7$ denote hydrogen, alkyl or aralkyl, it being possible for $R_4$ and/or $R_5$ to be bonded to the o-position of the benzene ring or to one another or for $R_6$ to be bonded to $R_7$, $R_8$ denotes alkyl or aryl, $R_9$ denotes hydrogen, alkyl or aralkyl, $R_{10}$ denotes hydrogen, alkyl, cyano, halogen or nitro, $R_{11}$ denotes amino or hydroxyl, $R_{12}$ denotes hydrogen, alkyl, aralkyl or aryl, $R_{13}$ denotes hydrogen, alkyl, halogen, cyano or alkoxycarbonyl and n denotes 1, 2 or 3, and wherein the substituents R–$R_{10}$, $R_{12}$ and $R_{13}$ can contain non-ionic substituents and/or a carboxyl group.

Non-ionic substituents in the sense of the present invention are the non-dissociating substituents customary in dyestuff chemistry, such as, for example, cyano, hydroxyl, halogen, such as fluorine, chlorine or bromine, nitro, alkyl, monoalkylamino and dialkylamino, phenyl, alkoxy, acyloxy, alkoxycarbonyl and alkoxycarbonyloxy, alkyl and alkoxy preferably containing 1–4 C atoms and acyl representing, in particular, $C_1$–$C_4$-alkylcarbonyl.

Examples of alkyl radicals within the scope of this invention are those with 1–8, in particular 1–4, C atoms. Examples of substituents of the alkyl radicals R–$R_{10}$, $R_{12}$ and $R_{13}$ are halogen, hydroxyl, $C_1$–$C_4$-alkoxy, phenyloxy, benzyloxy, $C_1$–$C_4$-alkoxycarbonyl, carboxyl, amidocarbonyl or cyano. Halogen preferably represents fluorine, chlorine and bromine. By alkenyl and alkinyl radicals, there are understood, in particular, those with 2–5 C atoms.

Cycloalkyl represents, for example, cyclopentyl or cyclohexyl, optionally substituted by $C_1$–$C_4$-alkyl.

Examples of suitable acyl radicals are $C_1$–$C_3$-alkylcarbonyl, benzoyl which is optionally substituted by halogen or $C_1$–$C_4$-alkyl, $C_1$–$C_4$-alkoxycarbonyl, mono- and di-$C_1$–$C_4$-alkylaminocarbonyl, benzylaminocarbonyl, $C_1$-$C_4$-alkylsulphonyl, phenylsulphonyl or di-$C_1$-$C_4$-alkylaminosulphonyl.

By aryl, there is preferably understood phenyl, and by aralkyl there are preferably understood benzyl and β-phenyl-$C_2$-$C_2$-alkyl. The phenyl rings can be substituted, for example by 1–3 non-ionic radicals, such as halogen, $C_1$-$C_4$-alkyl, $C_1$-$C_4$-alkoxy, $C_1$-$C_4$-alkoxycarbonyl, carboxyl, amidocarbonyl, cyano, nitro, amidosulphonyl, $C_1$-$C_3$-alkylcarbonylamino or benzoylamino.

The radicals $R/R_1$, $R_4/R_5$ and $R_6/R_7$, together with the nitrogen atom to which they are bonded, preferably form a 5-membered or 6-membered ring, such as pyrrolidine, piperidine, morpholine, piperazine, N-methyl-piperazine or N-hydroxyethyl-piperazine.

Examples of suitable heterocyclic radicals R are the 2-thienyl, 2-furyl and 2-tetrahydrofuryl radical.

If the radicals $R_4$ and/or $R_5$ are bonded to the o-position of the benzene ring to which they are linked via the nitrogen atom, they form, for example, together with the nitrogen atom and the benzene ring, a dihydroindole, tetrahydroquinoline, tetrahydroquinoxaline or tetrahydro-1,4-benzoxazine ring, optionally substituted by 1–4 $C_1$-$C_4$-alkyl groups.

Possible anionic radicals An are the organic and inorganic anions which are customary for cationic dyestuffs.

Examples of inorganic anions are fluoride, chloride, bromide and iodide, perchlorate, hydroxyl, radicals of acids containing S, such as bisulphate, sulphate, disulphate and aminosulphate; radicals of nitrogen-oxygen acids, such as nitrate; radicals of oxygen acids of phosphorus, such as dihydrogen phosphate, hydrogen phosphate, phosphate and metaphosphate; radicals of carbonic acid, such as bicarbonate and carbonate; further anions of oxygen acids and complex acids, such as methosulphate, ethosulphate, cyanate, thiocyanate, trichlorozincate and tetrachlorozincate, tribromozincate and tetrabromozincate, stannate, borate and tetrafluoborate, as well as anions of esters of boric acid, such as of the glycerol ester of boric acid, and of esters of phosphoric acid, such as of methylphosphate.

Examples of organic anions are anions of saturated or unsaturated aliphatic, cycloaliphatic, aromatic and heterocyclic carboxylic acids and sulphonic acids, such as radicals of acetic acid, chloroacetic acid, cyanoacetic acid, hydroxyacetic acid, aminoacetic acid, methylaminoacetic acid, aminoethyl-sulphonic acid, methylaminoethyl-sulphonic acid, propionic acid, 3-chloropropionic acid, 2-hydroxypropionic acid, 3-hydroxypropionic acid, O-ethylglycollic acid, glyceric acid, 3-(nonyloxy)-propionic acid, the etherpropionic acid of the alcohol mixture with 6–10 carbon atoms, nonylphenol-tetraethylene glycol-ether-propionic acid, nonylphenol-diethylene glycol-ether-propionic acid, dodecyltetraethylene glycol-ether-propionic acid, phenoxyacetic acid, 2,2,2-trimethylacetic acid, n-caproic acid, 2-ethyl-n-caproic acid, stearic acid, oleic acid, ricinoleic acid, palmitic acid, n-pelargonic acid, lauric acid, a mixture of aliphatic carboxylic acids with 9–11 carbon atoms (Versatic Acid 911 from Shell), a mixture of aliphatic carboxylic acids with 15–19 carbon atoms (Versatic Acid 1519 from Shell), coconut fatty acid first runnings, undecanecarboxylic acid, n-tridecanecarboxylic acid and a coconut fatty acid mixture; acrylic acid, methacrylic acid, crotonic acid, propargylic acid, oxalic acid, malonic acid, succinic acid, glutaric acid, adipic acid, pimelic acid, suberic acid, azelaic acid, the isomer mixture of 2,2,4- and 2,4,4-trimethyladipic acid, sebacic acid, isoebacic acid (isomer mixture), tartaric acid, citric acid, glyoxylic acid, dimethyl ether-α,α'-dicarboxylic acid, methylene-bis-thioglycollic acid, dimethyl sulphide-α,α-dicarboxylic acid, 2,2'-dithio-di-n-propionic acid, fumaric acid, maleic acid, ethyl-bis-iminoacetic acid, methanesulphonic acid, ethanesulphonic acid, 2-hydroxyethanesulphonic acid and Mersolat, that is to say $C_8$-$C_{15}$ paraffinsulphonic acid, obtained by chlorosulphonation of liquid paraffin.

Examples of suitable anions of cycloaliphatic carboxylic acids are the anions of cyclohexanecarboxylic acid and cyclohexene-3-carboxylic acid, and examples of anions of araliphatic monocarboxylic acids are the anions of phenylacetic acid, 4-methylphenylacetic acid and mandelic acid.

Examples of suitable anions of aromatic carboxylic acids are the anions of benzoic acid, 2-methylbenzoic acid, 3-methylbenzoic acid, 4-methylbenzoic acid, 4-tert.-butylbenzoic acid, 2-bromobenzoic acid, 2-chlorobenzoic acid, 3-chlorobenzoic acid, 4-chlorobenzoic acid, 2,4-dichlorobenzoic acid, 2,5-dichlorobenzoic acid, 2-nitrobenzoic acid, 3-nitrobenzoic acid, 4-nitrobenzoic acid, 2-chloro-4-nitrobenzoic acid, 6-chloro-3-nitro-benzoic acid, 2,4-dinitrobenzoic acid, 3,4-dinitrobenzoic acid, 3,5-dinitrobenzoic acid, 2-hydroxybenzoic acid, 3-hydroxbenzoic acid, 4-hydroxybenzoic acid, 2-mercaptobenzoic acid, 4-nitro-3-methylbenzoic acid, 4-aminobenzoic acid, 5-nitro-2-hydroxybenzoic acid, 3-nitro-2-hydroxybenzoic acid, 4-methoxybenzoic acid, 3-nitro-4-methoxybenzoic acid, 4-chloro-3-hydroxybenzoic acid, 3-chloro-4-hydroxybenzoic acid, 5-chloro-2-hydroxy-3-methylbenzoic acid, 4-ethylmercapto-2-chlorobenzoic acid, 2-hydroxy-3-methylbenzoic acid, 6-hydroxy-3-methylbenzoic acid, 2-hydroxy-4-methylbenzoic acid, 6-hydroxy-2,4-dimethylbenzoic acid, 6-hydroxy-3-tert.-butylbenzoic acid, phthalic acid, tetrachlorophthalic acid, 4-hydroxyphthalic acid, 4-methoxyphthalic acid, isophthalic acid, 4-chloroisophthalic acid, 5-nitro-isophthalic acid, terephthalic acid, nitroterephthalic acid and diphenyl-3,4-carboxylic acid, o-vanillic acid, 3-sulphobenzoic acid, benzene-1,2,4,5-tetracarboxylic acid, naphthalene-1,4,5,8-tetracarboxylic acid, biphenyl-4-carboxylic acid, abietic acid, phthalic acid mono-n-butyl ester, terephthalic acid monomethyl ester, 3-hydroxy-5,6,7,8-tetrahydronaphthalene-2-carboxylic acid, 2-hydroxy-1-naphthoic acid and anthraquinone-2-carboxylic acid.

Examples of suitable anions of heterocyclic carboxylic acids are the anions of pyromucic acid, dehydromucic acid and indolyl-3-acetic acid.

Examples of suitable anions of aromatic sulphonic acids are the anions of benzenesulphonic acid, benzene-1,3-disulphonic acid, 4-chlorobenzenesulphonic acid, 3-nitrobenzenesulphonic acid, 6-chloro-3-nitrobenzenesulphonic acid, toluene-4-sulphonic acid, toluene-2-sulphonic acid, toluene-ω-sulphonic acid, 2-chlorotoluene-4-sulphonic acid, 1-hydroxybenzenesulphonic acid, n-dodecylbenzenesulphonic acid, 1,2,3,4-tetrahydronaphthalene-6-sulphonic acid, naphthalene-1-sulphonic acid, naphthalene-1,4- or -1,5-disulphonic acid, naphthalene-1,3,5-trisulphonic acid, 1-naphthol-2-sulphonic acid, 5-nitronaphthalene-2-sulphonic acid, 8-aminonaphthalene-1-sulphonic acid, stilbene-2,2'-disulphonic acid and biphenyl-2-sulphonic acid.

Colourless anions are preferred. For dyeing from an aqueous medium, anions which do not excessively impair the solubility of the dyestuff in water are preferred. For dyeing from organic solvents, anions which assist the solubility of the dyestuff in organic solvents or at least do not influence it adversely are frequently also preferred.

The anion is in general decided by the preparation process and by the purification of the crude dyestuff which may be carried out. In general the dyestuffs are in the form of halides (especially chlorides or bromides) or methosulphates, ethosulphates, sulphates, benzenesulphonates or toluenesulphonates, or acetates. The anions can be replaced by other anions in a known manner.

Of the dyestuffs of the formula II, those of the formula

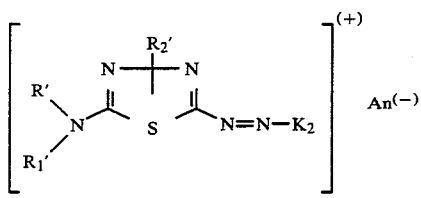

wherein

R' denotes hydrogen, a $C_1-C_8$-alkyl radical which is optionally substituted by hydroxyl, halogen, cyano, $C_1-C_4$-alkoxy, carboxyl, aminocarbonyl or $C_1-C_4$-alkoxycarbonyl, a $C_2-C_4$-alkenyl radical, a cyclohexyl radical which is optionally substituted by $C_1-C_4$-alkyl, a phenyl, benzyl or phenylethyl radical which is optionally substituted by halogen, $C_1-C_4$-alkyl or $C_1-C_4$-alkoxy, a $C_1-C_4$-alkoxycarbonyl, mono- or di-$C_1-C_4$-alkylaminocarbonyl, aminocarbonyl, mono- or di-$C_1-C_4$-alkylaminosulphonyl, 2-thienyl, 2-furyl, 2-tetrahydrofuryl, amino, $C_1-C_4$-alkylamino or di-($C_1-C_4$-alkyl)-amino radical or a phenylamino or benzylamino radical which is optionally substituted by $C_1-C_4$-alkyl or $C_1-C_4$-alkoxy, $R_1'$ denotes a $C_1-C_8$-alkyl radical which is optionally substituted by hydroxyl, halogen, cyano, $C_1-C_4$-alkoxy, carboxyl, aminocarbonyl- or $C_1-C_4$-alkoxycarbonyl, a $C_2-C_4$-alkenyl radical or a benzyl or phenylethyl radical which is optionally substituted by halogen, $C_1-C_4$-alkyl or $C_1-C_4$-alkoxy, $R_2$ denotes a $C_1-C_8$-alkyl radical which is optionally substituted by hydroxyl, halogen, cyano, $C_1-C_4$-alkoxy, carboxyl, aminocarbonyl or $C_1-C_4$-alkoxycarbonyl, a $C_2-C_4$-alkenyl radical or a benzyl or phenylethyl radical which is optionally substituted by halogen, $C_1-C_4$-alkyl or $C_1-C_4$-alkoxy, $K_2$ denotes a coupling component of the formula

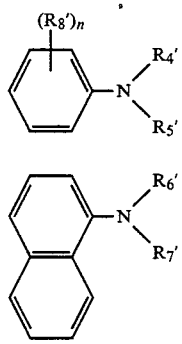

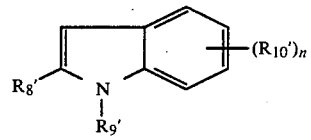

or

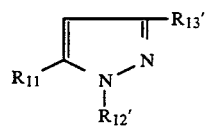

$R_3'$ denotes hydrogen, a $C_1-C_4$-alkyl radical which is optionally substituted by halogen, a $C_1-C_4$-alkoxy radical or halogen, $R_4'$ and $R_6'$ denote hydrogen, a $C_1-C_8$-alkyl radical which is optionally substituted by hydroxyl, halogen, cyano, $C_1-C_4$-alkoxy, carboxyl, aminocarbonyl or $C_1-C_4$-alkoxycarbonyl, or a benzyl or phenylethyl radical which is optionally substituted by halogen, $C_1-C_4$-alkyl or $C_1-C_4$-alkoxy, $R_5'$ and $R_7'$ denote a $C_1-C_8$-alkyl radical which is optionally substituted by hydroxyl, halogen, cyano, $C_1-C_4$-alkoxy, carboxyl, aminocarbonyl or $C_1-C_4$-alkoxycarbonyl, or a phenyl, benzyl or phenylethyl radical which is optionally substituted by halogen, $C_1-C_4$-alkyl or $C_1-C_4$-alkoxy, $R_8'$ denotes a $C_1-C_8$-alkyl radical which is optionally substituted by hydroxyl, halogen, cyano, $C_1-C_4$-alkoxy, carboxyl, aminocarbonyl or $C_1-C_4$-alkoxycarbonyl, or a phenyl radical which is optionally substituted by halogen, $C_1-C_4$-alkyl or $C_1-C_4$-alkoxy, $R_9'$ denotes hydrogen, a $C_1-C_8$-alkyl radical which is optionally substituted by hydroxyl, halogen, cyano, $C_1-C_4$-alkoxy, carboxyl, aminocarbonyl or $C_1-C_4$-alkoxycarbonyl, or a benzyl or phenylethyl radical which is optionally substituted by halogen, $C_1-C_4$-alkyl or $C_1-C_4$-alkoxy, $R_{10}'$ denotes hydrogen, a $C_1-C_8$-alkyl radical which is optionally substituted by hydroxyl, halogen, cyano, $C_1-C_4$-alkoxy, carboxyl, aminocarbonyl or $C_1-C_4$-alkoxycarbonyl, cyano, halogen or nitro, $R_{12}'$ denotes hydrogen, $C_1-C_4$-alkyl or a phenyl or benzyl radical which is optionally substituted by halogen, $C_1-C_4$-alkyl, $C_1-C_4$-alkoxy or nitro and $R_{13}'$ denotes hydrogen, methyl, halogen, cyano, methoxycarbonyl or ethoxycarbonyl, wherein R' with $R_1'$ and $R_4'$ with $R_5'$ and $R_6'$ and $R_7'$ can be linked to form a pyrrolidine, piperidine, morpholine or piperazine ring which is optionally substituted by $C_1-C_4$-alkyl, and wherein $R_4'$ and/or $R_5'$ can be bonded to the o-position of the benzene ring and can then form, together with the benzene ring and the nitrogen atom, a dihydroindole, tetrahydroquinoline, tetrahydroquinoxaline or tetrahydro-1,4-benzoxazine ring which is optionally substituted by $C_1-C_4$-alkyl, and n, $R_{11}$ and $An^{(-)}$ have the meaning for formula II, are to be mentioned in particular.

Particularly preferred dyestufs have the general formula

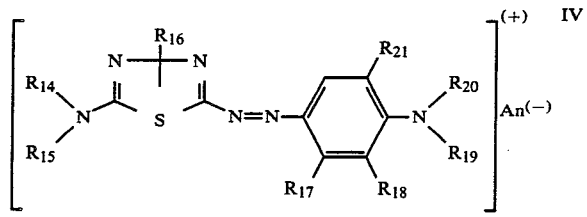

wherein $R_{14}$ denotes H, —CH$_3$, C$_2$H$_5$, —C$_3$H$_7$, iso—C$_3$H$_7$, —C$_4$H$_9$, iso—C$_4$H$_9$, sec.—C$_4$H$_9$, tert.—C$_4$H$_9$,

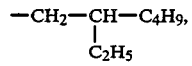

—C$_2$H$_4$OH, —CH$_2$—CHOH—CH$_3$, —C$_2$H$_4$CN, —C$_6$H$_{11}$, —C$_5$H$_9$, —CH$_2$—C$_6$H$_5$, —C$_6$H$_5$, —C$_6$H$_4$-Cl—(p), C$_6$H$_3$Cl$_2$—(2,5), C$_6$H$_4$—CH$_3$—(o, m or p), —C$_6$H$_4$—OCH$_3$—(p), —C$_2$H$_4$—O—CH$_3$, C$_2$H$_4$—O—C$_2$H$_5$,

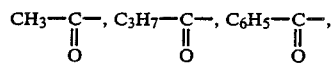

4—Cl—C$_6$H$_4$—CO, 4—CH$_3$—C$_6$H$_4$—CO, C$_2$H$_5$OCO—, CH$_3$OCO—, C$_2$H$_5$NHCO—, (C$_2$H$_5$)$_2$NCO—, (C$_2$H$_5$)$_2$NSO$_2$—, CH$_3$NHSO$_2$— or H$_2$NCO—, $R_{15}$ denotes —CH$_3$, —C$_2$H$_5$, —C$_3$H$_7$, iso—C$_3$H$_7$, —C$_4$H$_9$, iso—C$_4$H$_9$, sec.—C$_4$H$_9$, tert.—C$_4$H$_9$,

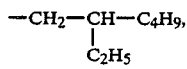

—C$_2$H$_4$OH, —CH$_2$—CHOH—CH$_3$, —C$_2$H$_4$CN, —C$_6$H$_{11}$, —C$_5$H$_9$, —CH$_2$—C$_6$H$_5$, —C$_2$H$_4$—O—CH$_3$ or —C$_2$H$_4$—O—C$_2$H$_5$, $R_{16}$ denotes alkyl with 1-4 C atoms, 2-cyanoethyl, 2-carbamoylethyl, 2-hydroxyethyl or benzyl, $R_{17}$ denotes hydrogen, methyl, ethyl, methoxy, ethoxy, chlorine or bromine, $R_{18}$ denotes hydrogen, fluorine, chlorine, bromine, methyl, ethyl, methoxy or ethoxy, $R_{19}$ denotes hydrogen, alkyl with 1-4 C atoms or benzyl and $R_{20}$ denotes hydrogen, alkyl with 1-4 C atoms, benzyl or phenyl, or $R_{19}$ and $R_{20}$, together with the N atom bonded to them, represent a saturated heterocyclic ring which can contain further hetero-atoms, mainly morpholine, piperidine, pyrrolidine or N-methyl-piperazine, or $R_{18}$ and $R_{19}$ and/or $R_{20}$ and $R_{21}$ together form a radical of the formula

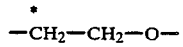  (a)

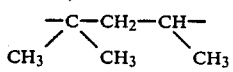  (b)

—CH—CH$_2$— (c)
  |
  CH$_3$ or

—CH$_2$—CH$_2$—CH$_2$— (d)

wherein the C atom marked x is bonded to the N atom, $R_{21}$ denotes hydrogen, fluorine, chlorine, bromine, methyl, ethyl, methoxy or ethoxy and An$^{\ominus}$ denotes an anion.

Dyestuffs which have the general formulae

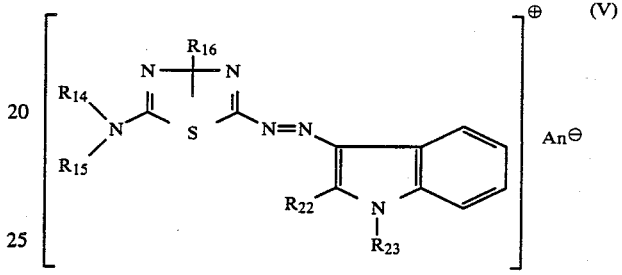

and

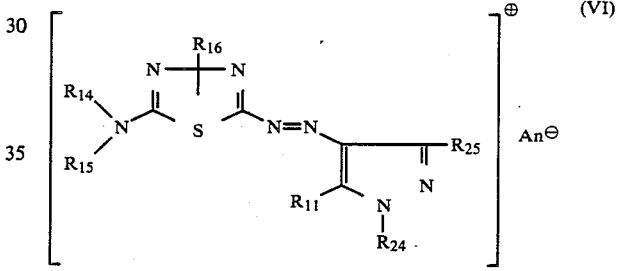

wherein $R_{11}$, $R_{14}$, $R_{15}$, $R_{16}$ and An$^{\ominus}$ have the meaning indicated above, $R_{22}$ denotes methyl, ethyl or phenyl, $R_{23}$ denotes hydrogen, methyl, β-cyanoethyl, β-carbamoylethyl and β-carboxyethyl, $R_{24}$ denotes hydrogen, methyl, ethyl, benzyl or phenyl which is optionally substituted by chlorine, methyl, methoxy or nitro and $R_{25}$ denotes hydrogen, methyl, halogen, cyano or methoxycarbonyl, are likewise preferred.

The dyestuffs of the formula I are prepared by a process in which a 2-amino-1,3,4-thiadiazole of the formula

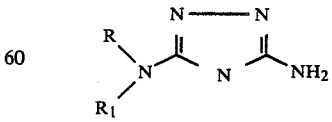

is diazotised, the diazotisation product is coupled with a coupling component of the formula

KH                                                                        VIII and the coupling product is reacted with a quaternising agent of the general formula $$R_2-X \qquad \text{IX}$$

wherein, in the formula VII to IX,

K and the radicals R to $R_3$ have the meaning indicated in formula I and

X denotes a group which can be split off as an anion $An^\ominus$.

Examples of suitable 2-amino-1,3,4-thiadiazole of the formula VII are: 2,5-diamino-1,3,4-thiadiazole, 5-methylamino-2-amino-1,3,4-thiadiazole, 5-ethylamino-2-amino-1,3,4-thiadiazole, 5-iso-propylamino-2-amino-1,3,4-thiadiazole, 5-sec.-butylamino-2-amino-1,3,4-thiadiazole, 5-(2-ethyl)-hexylamino-2-amino-1,3,4-thiadiazole, 5-benzylamino-2-amino-1,3,4-thiadiazole, 5-phenethylamino-2-amino-1,3,4-thiadiazole, 5-cyclohexylamino-2-amino-1,3,4-thiadiazole, 5-2-chloroethylamino-2-amino-1,3,4-thiadiazole, 5-2-hydroxyethylamino-2-amino-1,3,4-thiadiazole, 5-2-methoxyethylamino-2-amino-1,3,4-thiadiazole, 5-2-hydroxypropylamino-2-amino-1,3,4-thiadiazole, 5-allylamino-2-amino-1,3,4-thiadiazole, 5-cyanoethylamino-2-amino-1,3,4-thiadiazole, 5-2-carbethoxyethylamino-2-amino-1,3,4-thiadiazole, 5-acetylamino-2-Amino-1,3,4-thiadiazole, 5-benzoylamino-2-amino-1,3,4-thiadiazole, 5-methoxycarbonylamino-2-amino-1,3,4-thiadiazole, 5-ethoxycarbonylamino-2-amino-1,3,4-thiadiazole, 5-ethylsulphonylamino-2-amino-1,3,4-thiadiazole, 5-ethylcarbonylamino-2-amino-1,3,4-thiadiazole, 5-diethylcarbonoylamino-2-amino-1,3,4-thiadiazole, 5-dimethylamino-2-amino-1,3,4-thiadiazole, 5-N-ethyl-N-methyl-amino-2-amino-1,3,4-thiadiazole, 5-N-hydroxyethyl-N-methylamino-2-amino-1,3,4-thiadiazole, 5-N-($\beta$-methoxyethyl)-N-methylamino-2-amino-1,3,4-thiadiazole, 5-N-($\beta$-ethoxyethyl)-N-methylamino-2-amino-1,3,4-thiadiazole, 5-N-($\beta$-cyanoethyl)-N-methylamino-2-amino-1,3,4-thiadiazole, 5-N-sec.-butyl-N-methylamino-2-amino-1,3,4-thiadiazole, 5-N-(2-ethylhexyl)-N-methylamino-2-amino-1,3,4-thiadiazole, 5-N-benzyl-N-methyl-amino-2-amino-1,3,4-thiadiazole, 5-N-phenyl-N-methyl-amino-2-amino-1,3,4-thiadiazole, 5-N-p-tolyl-N-methylamino-2-amino-1,3,4-thiadiazole, 5-N-(p-methoxyphenyl)-N-methylamino-2-amino-1,3,4-thiadiazole, 5-diethylamino-2-amino-1,3,4-thiadiazole, 5-N-$\beta$-cyanoethyl-N-ethylamino-2-amino-1,3,4-thiadiazole, 5-N-$\beta$-hydroxyethyl-N-ethylamino-2-amino-1,3,4-thiadiazole, 5-N-benzyl-N-ethylamino-2-amino-1,3,4-thiadiazole, 5-N-$\beta$-methoxyethyl-N-ethylamino-2-amino-1,3,4-thiadiazole, 5-N-$\beta$-ethoxyethyl-N-ethylamino-2-amino-1,3,4-thiadiazole, 5-di-tert.-butylamino-2-amino-1,3,4-thiadiazole, 5-di-(2-ethylhexyl)-amino-2-amino-1,3,4-thiadiazole, 5-N-phenyl-N-ethylamino-2-amino-1,3,4-thiadiazole, 5-di-($\beta$-metoxyethyl)-amino-2-amino-1,3,4-thiadiazole, 5-pyrrolidino-2-amino-1,3,4-thiadiazole, 5-piperidino-2-amino-1,3,4-thiadiazole, 5-morpholino-2-amino-1,3,4-thiadiazole, 5-N-methylpiperazino-2-amino-1,3,4-thiadiazole, 5-N-hydroxyethyl-piperazino-2-amino-1,3,4-thiadiazole, 5-diallylamino-2-amino-1,3,4-thiadiazole, 5-($\alpha$-methylhydrazino)-2-amino-1,3,4-thiadiazole and 5-($\beta$-phenylhydrazino)-2-amino-1,3,4-thiadiazole.

The invention also relates to 2-amino-1,3,4-thiadiazoles of the formula

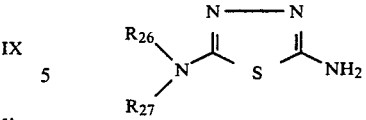

wherein $R_{26}$ denotes an alkyl, alkenyl, aryl, aralkyl, cycloalkyl, amino, alkylamino, dialkylamino, arylamino, aralkylamino or heterocyclic radical and $R_{27}$ denotes an alkyl, alkenyl or aralkyl radical, or $R_{26}$ and $R_{27}$ are linked to form a heterocyclic ring, their preparation and their use for the preparation of pharmaceuticals, agents for protecting plants and dyestuffs, for example dyestuffs of the formula I.

Examples of the substituents $R_{26}$ and $R_{27}$ correspond to the examples mentioned above for the radicals R and $R_1$. Examples of the compounds X are given with the examples of the compounds VII.

Thiadiazoles of the formula

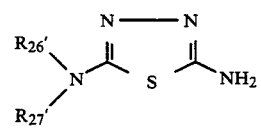

wherein $R_{26}'$ denotes a $C_1$-$C_8$-alkyl radical which is optionally substituted by hydroxyl, halogen, cyano, $C_1$-$C_4$-alkoxy, carboxyl, aminocarbonyl or $C_1$-$C_4$-alkoxycarbonyl, a $C_2$-$C_4$-alkenyl radical, a cyclohexyl radical which is optionally substituted by $C_1$-$C_4$-alkyl, a phenyl, benzyl or phenylethyl radical which is optionally substituted by halogen, $C_1$-$C_4$-alkyl or $C_1$-$C_4$-alkoxy, a $C_1$-$C_2$-alkylcarbonyl, $C_1$-$C_4$-alkoxycarbonyl, mono- or di-$C_1$-$C_4$-alkylaminocarbonyl, aminocarbonyl, mono- or di-$C_1$-$C_4$-alkylaminosulphonyl, 2-thienyl, 2-furyl, 2-tetrahydrofuryl, amino, $C_1$-$C_4$-alkylamino or di-($C_1$-$C_4$-alkyl)-amino radical or a phenylamino or benzylamino radical which is optionally substituted by $C_1$-$C_4$-alkyl or $C_1$-$C_4$-alkoxy and $R_{27}'$ denotes a $C_1$-$C_8$-alkyl radical which is optionally substituted by hydroxyl, halogen, cyano, $C_1$-$C_4$-alkoxy, carboxyl, aminocarbonyl- or $C_1$-$C_4$-alkoxycarbonyl, a $C_2$-$C_4$-alkenyl radical or a benzyl or phenylethyl radical which is substituted by halogen, $C_1$-$C_4$-alkyl or $C_1$-$C_4$-alkoxy, are to be singled out.

The compounds of the formula X can be prepared by reacting compounds of the formula

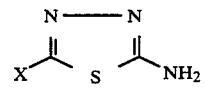

wherein X denotes a group which can be split off as an anion, with amines of the formula

Examples which may be mentioned of groups which can be split off as anions are halogen, such as fluorine, chlorine or bromine, alkylsulphonyl or aralkylsulphonyl.

The reaction can be carried out without a solvent or in water, organic solvents or aqueous-organic solvents, in the presence of an acid-binding agent. An excess of amine XIII can also be used as the solvent and/or acid-binding agent.

Preferred possible organic solvents are alcohols, such as ethanol, and possible acid-binding agents are tertiary or cyclic amines, such as trialkylamines or pyridines, or alkali metal oxides or hydroxides and alkaline earth metal oxides or hydroxides, such as magnesium oxide.

The reaction temperatures are preferably 30°–150° C., in particular 70°–100° C.

Examples of suitable coupling components of the formula VIII are: N,N-dimethylaniline, N,N-diethylaniline, N-methyl-N-n-butyl-aniline, N,N-diethyl-m-toluidine, N,N-diethylamino-3-chlorobenzene, N,N-diethylamino-3-methoxybenzene, 1-N,N-diethylamino-2,5-dimethoxybenzene, 1-N,N-diethylamino-2,5-diethoxybenzene, N-ethyl-N-β-chloroethylaniline, N,N-bis-(β-chloro-ethyl)-aniline, N-(β-chloroethyl)-N-butyl-aniline, N-(β-chloro-ethyl)-N-ethyl-m-toluidine, N,N-bis-(β-chloroethyl)-m-toluidine, N-methyl-N-β-hydroxyethyl-aniline, N-ethyl-N-β-hydroxyethylaniline, N,N-bis-(β-hydroxyethyl)-aniline, N-butyl-N-(β-hydroxyethyl)-aniline, N,N-bis-(β-γ-dihydroxypropyl)-aniline, N-ethyl-N-benzylaniline, N-ethyl-N-benzyl-m-toluidine, N-ethyl-N-β-hydroxyethyl-m-toluidine, N,N-bis-(β-hydroxyethyl)-m-toluidine, 1-N-ethyl-N-β-hydroxyethylamino-2-methoxy-5-methylbenzene, N-ethyl-N-β-acetoxyethylaniline, N,N-bis-(β-acetoxyethyl)-aniline, N-butyl-N-β-acetoxyethyl-aniline, N-ethyl-N-β-acetoxyethyl-m-toluidine, N,N-bis-(β-acetoxyethyl)m-toluidine, 1-N-ethyl-N-β-acetoxyethylamino-2-methoxy-5-methylbenzene, N,N-bis-(β-ethoxycarbonyloxyethyl)-aniline, N,N-bis-(β-methoxy-carbonyloxyethyl)-aniline, N,N-bis-(β-ethoxycarbonyloxyethyl)-m-toluidine, N,N-bis-(β-methoxycarbonyloxyethyl)-m.toluidine, N-methyl-N-β-cyanoethyl-aniline, N,N-bis-(β-cyanoethyl)-aniline, N-ethyl-N-β-cyanoethyl-m-toluidine, N-β-hydroxyethyl-N-β-cyanoethyl-aniline, N-β-acetoxy-ethyl-N-β-cyanoethyl-m-toluidine, N-ethyl-2-methoxy-5-methylaniline, N-β-cyanoethyl-2-methoxy-5-methyl-aniline, N-β-cyanoethyl-2-ethoxy-5-methyl-aniline, N-β-cyanoethyl-2,5-dimethyl-aniline, N-methyl-aniline, N-ethyl-aniline, N-n-butyl-aniline, N-β-cyanoethyl-aniline, N-β-chloroethylaniline, n-β-hydroxyethyl-aniline, N-β-acetoxyethyl-aniline, N-β-methoxy- and N-β-ethoxy-carbonyloxyethyl-aniline, N-β-carbomethoxyethyl-aniline, N-β-cyanoethyl-2-methyl-aniline, N-methyl-m-toluidine, N-ethyl-m-toluidine, N-β-cyanoethyl-m-toluidine, N-β-chloroethyl-m-toluidine, N-β-hydroxyethyl-m-toluidine, N-β-acetoxyethyl-m-toluidine, N-β-methoxycarbonyloxyethyl-m-toluidine, N-ethyl-3-ethyl-aniline, N-n-propyl-3-ethyl-aniline, N-β-cyanoethyl-3-ethyl-aniline, N-β-cyanoethyl-3-methoxy-aniline, N-β-chloroethyl-3-methoxyaniline, N-β-cyanoethyl-3-ethoxy-aniline, N-β-chloroethyl-3-ethoxy-aniline, N-ethyl-3-chloro-aniline, N-β-cyanoethyl-3-chloro-aniline, N-β-chloroethyl-3-chloroaniline, N-β-hydroxyethyl-3-chloro-aniline, N-β-acetoxyethyl-3-chloroaniline, N-β-cyanoethyl-3-bromo-aniline, diphenylamine, N-methyl-diphenylamine, N-ethyl-diphenylamine, N-propyl-diphenylamine, N,N-dimethyl-α-naphthylamine, N,N-diethyl-α-naphthylamine, N-ethyl-N-β-cyanoethyl-α-naphthylamine, N-ethyl-N-β-hydroxyethyl-α-naphthylamine, N,N-dipropyl-α-naphthylamine, N-butyl-N-β-hydroxyethyl-α-naphthylamine, N-ethyl-N-benzyl-α-naphthylamine, N-ethyl-N-(2-phenyl-ethyl)-α-naphthylamine, N-ethyl-α-naphthylamine, N-phenyl-α-naphthylamine, N-propyl-α-naphthylamine, 2-methylindole, 2-phenylindole, 1-methyl-2-phenylindole, 1,2-dimethylindole, 1-β-cyanoethyl-2-methylindole, 1-β-cyanoethyl-2-phenylindole, γ-(2-phenylindol-1-yl)-propionic acid amide, γ-(2-methylindol-1-yl)-propionic acid amide, γ-(2-methylindol-1-yl)propionic acid, 2-β-naphthyl-indole, 2-p-biphenylylindole, 2,5-dimethylindole, 2,4-dimethyl-7-methoxyindole, 2-phenyl-5-ethoxyindole, 2-methyl-5-ethoxyindole, 2-methyl-5-chloroindole, 2-methyl-6-chloroindole, 2-methyl-5-nitroindole, 2-methyl-5-cyanoindole, 2-methyl-7-chloroindole, 2-methyl-5-fluoroindole, 2-methyl-5-bromoindole, 2-methyl-5,7-dichloroindole, 1-β-cyanoethyl-2,6-dimethylindole, o-toluidine, N-methyl-o-toluidine, N,N-dimethyl-o-toluidine, N-cyanoethyl-o-toluidine, N-methyl-N-cyanoethyl-o-toluidine, N-ethyl-o-toluidine, N-hydroxyethyl-o-toluidine, N,N-diethyl-o-toluidine, N-ethyl, N-cyanoethyl-o-toluidine, N-(β-chloroethyl)-o-toluidine N-(β-chloroethyl)-N-ethyl-o-toluidine, N-(β-chloroethyl)-N-methyl-o-toluidine, N-bis-(β-hydroxyethyl)-o-toluidine, N-bis-(β-hydroxypropyl)-o-toluidine, N-methyl-N-β-acetoxyethyl-o-toluidine, N-ethyl-N-acetaxyethyl-o-toluidine, N-methyl-N-(β-methoxy-carbonyloxyethyl)-o-toluidine, N-ethyl-N-(β-ethoxy-carbonyloxyethyl)-o-toluidine, N-bis-(β-methoxy-carbonyloxyethyl)-o-toluidine, N-methyl-N-benzyl-o-toluidine, N-methyl-N-(α-phenoxyethyl)-o-toluidine, N-methyl-2-fluoro-aniline, N-dimethyl-2-fluoroaniline, N-ethyl-2-fluoro-aniline, N-(β-chloroethyl)-2-fluoro-aniline, N-(β-hydroxyethyl)-2-fluoroaniline, N-ethyl-N-hydroxyethyl-2-fluoro-aniline, N-(β-acetoxy-ethyl)-2-fluoro-aniline, julolidine, 3-hydroxy-julolidine, 5-methyl-julolidine, 3-hydroxy-5-methyl-julolidine, 5-chloro-julolidine, N-methyltetrahydroquinoline, N-ethyl, 2,2,4-trimethyltetrahydroquinoline, 1,2,2,4-tetramethyl-tetrahydroquinoline, 1,2-dimethylindolenine, N-methyl-benzomorpholine, N-phenylmorpholine, N-phenyl-pyrrolidine, N-phenyl-piperidine, N-(2-methylphenyl)pyrrolidine, N-(2-fluorophenyl)-pyrrolidine, N,N-dimethyl-2-methoxy-aniline, N,N-dimethyl-2-ethoxy-aniline, N,N-dibutyl-2-methoxy-aniline, 1-phenyl-3-methyl-pyrazol-5-one, 1-(2-chlorophenyl)-3-methyl-pyrazol-5-one, 1-(3-chlorophenyl)-3-methyl-pyrazol-5-one, 1-(2,5-dichlorophenyl)-3-methylpyrazol-5-one, 1-(2-nitrophenyl)-3-methyl-pyrazol-5-one, 1-(3-nitrophenyl)-3-methyl-pyrazol-5-one, 1-(p-tolyl)-3-methyl-pyrazol-5-one, 1-benzyl-3-methyl-pyrazol-5-one, 1-(3-sulpholanyl)-3-methyl-pyrazol-5-one, 1-phenyl-pyrazol-5-one-3-carboxylic acid amide, 1-phenyl-pyrazol-5-one-3-carboxylic acid ethyl ester, 1-phenyl-3-methoxycarbonylmethyl-pyrazol-B 5-one, 1-β-cyanoethyl-3-methyl-pyrazol-5-one, 1-β-chloroethyl-3-ethyl-pyrazol-5-one, 1-β-acetoxyethyl-3-ethylpyrazol-5-one. 1-phenyl-3-methyl-5-aminopyrazole, 1-phenyl-5-aminopyrazole, 1-methyl-5-aminopyrazole, 1-ethyl-5-aminopyrazole, 1-benzyl-5-aminopyrazole, 1-phenyl-3-bromo-5-aminopyrazole, 1-methyl-3-methyl-5-aminopyrazole, 1-(p-tolyl)-5-aminopyrazole, 1-(3-nitrophenyl)-5-aminopyrazole, 5-aminolpyrazole and 1-(2-chlorophenyl)-5-aminopyrazole.

Possible quaternising agents are alkyl halides, halogenoacetamides, β-halogenopropionitriles, halogenohydrins, alkylene oxides, alkyl esters of sulphuric acid or alkyl esters of organic sulphonic acid, for example methyl chloride, bromide or iodide, ethyl chloride, bromide or iodide, propyl bromide or iodide, benzyl chloride or bromide, chloroacetamide, β-chloropropionitrile, ethylene chlorohydrin, dimethyl sulphate, diethyl sulphate, benzenesulphonic acid methyl ester, p-toluenesulphonic acid methyl, ethyl apropyl or butyl ester, allyl chloride or bromide, methallyl chloride or bromide, trimethyloxonium borofluoride, propargyl chloride, 1,4-dichloroprop-2-ene, 1-chloro-but-2-ene, 1-chloro-but-3-ine, 1,2-dichloro-prop-2-ene, 1-chloro-2-vinyl-prop-2-ene, 1-chloro-penta-2,4-diene and acrylonitrile, acrylic acid, acrylic acid amide and acrylic acid methyl ester.

The diazotisation of the 2-amino-1,3,4-thiadiazoles, of the formula V is carried out in a manner which is in itself known, for example with nitrosylsulphuric acid in 85% strength phosphoric acid or in mixtures of 85% strength phosphoric acid and acetic acid. The coupling of the diazotised 2-amino-1,3,4-thiadiazoles with the coupling components VI is likewise carried out in a manner which is in itself known, for example in an acid aqueous or aqueous-organic medium.

The quaternisation is appropriately carried out in an inert organic solvent, for example in a hydrocarbon, chlorohydrocarbon or nitrohydrocarbon, such as benzene, toluene, xylene, tetrachloroethane, chloroform, carbon tetrachloride, monochlorobenzene or dichlorobenzene or nitrobenzene, in an acid amide or acid anhydride, such as dimethylformamide, N-methylacetamide or acetic anhydride, in dimethylsulphoxide or in a ketone, such as acetone or methyl ethyl ketone. Instead of an organic solvent, it is also possible to use an excess of the alkylating agent. The quaternisation is carried out at elevated temperature, acid-binding agents, such as magnesium oxide, magnesium carbonate, sodium carbonate, calcium carbonate or sodium bicarbonate being added if appropriate, and if appropriate under pressure. The most favourable conditions in each case can easily be determined by a preliminary experiment.

The quaternised dyestuffs formed are sparingly soluble in the solvents used and can be isolated by filtration. If the quaternised dyestuffs remain partly or completely in solution when dimethylformamide, dimethylsulphoxide or acetonitrile is used, they can be separated out by diluting the solution with water and adding water-soluble salts, for example sodium chloride or potassium chloride.

The dyestuffs obtained by this process are outstandingly suitable for dyeing and printing fibres, which can be dyed with cationic dyestuffs, of polymers and copolymers of acrylonitrile and of dicyanoethylene, and acid-modified fibres of polyamide and polyester, fast colour shades being obtained. The dyestuffs can also be used for dyeing and printing tannin-treated cellulose materials, silk and leather. They are furthermore suitable for the preparation of writing fluids, products for use with rubber stamps and ball-point pen pastes and can also be used in flexographic printing.

Materials which are particularly suitable for dyeing with the basic dyestuffs of the general formula (I) are flocks, fibres, filaments, silvers, woven fabrics or knitted fabrics consisting of polyacrylonitrile or of copolymers of acrylonitrile, containing an acrylonitrile proportion of at least 85%, with other vinyl compounds, such as vinyl chloride, vinylidene chloride, vinyl fluoride, vinyl acetate, vinylpyridine, vinylimidazole, vinyl alcohol, acrylic acid esters and amides and methacrylic acid esters, and amides, and asymmetric dicyanoethylene. Flocks, fibres, filaments, slivers, woven fabrics or knitted fabrics consisting of acid-modified synthetic materials, in particular of acid-modified aromatic polyesters and acid-modified polyamide fibres, can likewise be excellently dyed. Examples of acid-modified aromatic polyesters are polycondensation products of sulphoterephthalic acid and ethylene glycol, that is to say polyethylene glycol terephthalates containing sulphonic acid groups (of the Dacron 64 type from Messrs. E. I. DuPont de Nemours and Company), such as are described in Belgian Patent Specification No. 549,179 and U.S. Pat. No. 2,893,816.

The dyeing can take place from a weakly acid liquor, the material appropriately being introduced into the dyebath at 40° to 60° C. and dyeing then being carried out at the boiling point. However, it is also possible to carry out the dyeing under pressure at temperatures above 100° C. Furthermore, the dyestuffs can be added to spinning solutions for the preparation of fibres containing polyacrylonitrile or can be applied to the non-stretched fibres.

The dyeings of the dyestuffs of the formula (I) according to the invention on materials consisting of polyacrylonitrile or acid-modified polyester fibres or polyamide fibres are distinguished by very good fastness to light, wet processing, rubbing and sublimation and by a high affinity for the fibre.

They are also distinguished by a relatively good migrating capacity and a low sensitivity to thiocyanate.

The dyestuffs can be used individually or in mixtures. They are very suitable for dyeing shaped articles made of polymers or copolymers of acrylonitrile, asymmetric dicyanoethylene, acid-modified aromatic polyesters or acid-modified synthetic high molecular weight polyamides in chlorohydrocarbons, as the dyebath, when they carry substituents which promote solubility in chlorohydrocarbons, such as, for example, the tert.-butyl group, or when the anion $An^{(-)}$ in the formula (I) is the anion of a monobasic organic acid with 4–30 carbon atoms.

Examples of such organic acids are: 2-ethylcaproic acid, lauric acid, oleic acid, linoleic acid, a mixture of aliphatic carboxylic acids with 15–19 carbon atoms (Versatic Acid 1519), a mixture of aliphatic carboxylic acids with 9–11 carbon atoms (Versatic Acid 911), coconut fatty acid first runnings, tetradecanoic acid, undecylenic acid, dimethylpropanoic acid, dimethylacetic acid, carboxylic acids, the carbon chain of which is interrupted by heteroatoms, such as nonylphenol-tetraethylene glycol ether-propionic acid, dodecyl-tetraethylene glycol ether-propionic acid, 3-(nonyloxy)-propionic acid, 3-(isotridecyloxy)-propionic acid, the ether-propionic acid of the alcohol mixture with 6–10 carbon atoms, nonylphenoxyacetic acid, aromatic carboxylic acids, such as tert.-butylbenzoic acid, cycloaliphatic carboxylic acids, such as hexahydrobenzoic acid, cyclohexenecarboxylic acid and abietic acid, and sulphonic acids, such as tetrapropylenebenzenesulphonic acid.

In the examples which follow, parts denote parts by weight.

EXAMPLE 1

10.5 parts of 2-amino-5-dimethylamino-1,3,4-thiadiazole are introduced into a mixture of 100 parts of 85% strength phosphoric acid and 30 parts of glacial acetic acid, the mixture is stirred at room temperature for ½ hour and 25 parts of nitrosylsulphuric acid are added dropwise at −5°. The mixture is subsequently stirred at 0° for 1 hour and the diazonium solution thus obtained is then allowed to run into a solution of 10.5 parts of N,N-dimethylaniline and 1 part of amidosulphonic acid in 130 parts of 10% strength hydrochloric acid at 0° and the mixture is buffered at pH 3 with sodium acetate solution. The dyestuff immediately couples completely. After filtering off and drying, 20 parts of the dyestuff of the formula

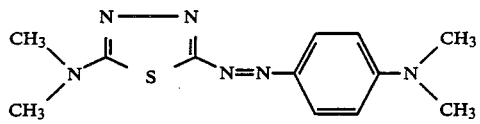

are obtained.

4.5 parts of this dyestuff are dissolved in 50 parts of glacial acetic acid containing 2 parts of magnesium oxide. 6 parts of dimethylsulphate are added and the solution is stirred at 60°–70° for 2 hours. After cooling, the reaction mixture is added to 200 parts of water, 1 part of Celite 545 is added and the aqueous acid solution is filtered through Celite 545. The dyestuff is isolated as the tetrachlorozincate in the customary manner, by adding salt up to a concentration of 20% and then adding zinc chloride. The tetrachlorozincate of the dyestuff has the structure:

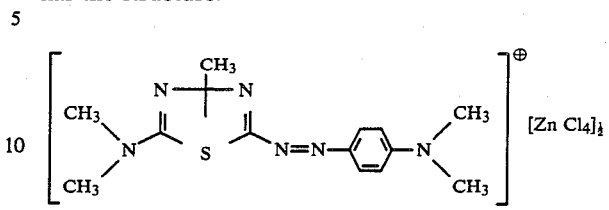

It dyes textile materials made of polyacrylonitrile and other textile materials which can be dyed with cationic dyestuffs in blue shades with outstanding fastness to light and wet processing, coupled with excellent affinity and good depth of colour as well as a relatively good migrating capacity.

If the procedure followed is as described in Example 1 and the diazo components and coupling components listed in the table which follows and the quaternising agents mentioned there are used, similar dyestuffs which dye polyacrylonitrile in the colour shades indicated, with similar fastness properties, are obtained.

| Example | Diazo component | Coupling component | Colour shade on polyacrylonitrile |
|---|---|---|---|
| 2 | (CH₃)₂N-C(=N-N=)S-C-NH₂ | C₆H₅-N(C₂H₅)₂ | blue |
| 3 | (CH₃)₂N-C(=N-N=)S-C-NH₂ | C₆H₅-N(C₂H₄OH)(CH₃) | blue |
| 4 | (CH₃)₂N-C(=N-N=)S-C-NH₂ | C₆H₅-N(C₃H₇)₂ | blue |
| 5 | (CH₃)₂N-C(=N-N=)S-C-NH₂ | C₆H₅-N(C₄H₉)₂ | blue |
| 6 | (CH₃)₂N-C(=N-N=)S-C-NH₂ | C₆H₅-N(C₂H₅)(CH₂-C₆H₅) | blue |
| 7 | (CH₃)₂N-C(=N-N=)S-C-NH₂ | C₆H₅-N(morpholino) | blue |

-continued

| # | Diazo component | Coupling component | Color |
|---|---|---|---|
| 8 | 2-amino-5-(dimethylamino)-1,3,4-thiadiazole | C₆H₅–N(CH₃)(C₂H₄–OCH₃) | blue |
| 9 | 2-amino-5-(dimethylamino)-1,3,4-thiadiazole | C₆H₅–N(C₂H₄–O–CO–CH₃)₂ | blue |
| 10 | 2-amino-5-(dimethylamino)-1,3,4-thiadiazole | C₆H₅–N(C₂H₄–O–CO–OCH₃)₂ | blue |
| 11 | 2-amino-5-(dimethylamino)-1,3,4-thiadiazole | 4-methyl-3,4-dihydro-2H-1,4-benzoxazine | blue |
| 12 | 2-amino-5-(dimethylamino)-1,3,4-thiadiazole | C₆H₅–N(C₂H₄–OCH₃)₂ | blue |
| 13 | 2-amino-5-(dimethylamino)-1,3,4-thiadiazole | 1-methyl-1,2,3,4-tetrahydroquinoline | blue |
| 14 | 2-amino-5-(dimethylamino)-1,3,4-thiadiazole | 1-ethyl-2,2,4-trimethyl-1,2,3,4-tetrahydroquinoline | blue |
| 15 | 2-amino-5-(dimethylamino)-1,3,4-thiadiazole | julolidine | blue |
| 16 | 2-amino-5-(dimethylamino)-1,3,4-thiadiazole | 8-methyljulolidine | blue |

-continued

| # | Diazo component | Coupling component | Color |
|---|---|---|---|
| 17 | 2-amino-5-(dimethylamino)-1,3,4-thiadiazole | 3-methyl-N,N-dimethylaniline | blue |
| 18 | 2-amino-5-(dimethylamino)-1,3,4-thiadiazole | 3-methyl-N-(2-hydroxyethyl)-N-ethylaniline | blue |
| 19 | 2-amino-5-(dimethylamino)-1,3,4-thiadiazole | 2-methyl-N,N-dimethylaniline | blue |
| 20 | 2-amino-5-(dimethylamino)-1,3,4-thiadiazole | 1,3-dimethyl-1,2,3,4-tetrahydroquinoline | blue |
| 21 | 2-amino-5-(dimethylamino)-1,3,4-thiadiazole | 1-methyl-1,2,3,4-tetrahydroquinoline | blue |
| 22 | 2-amino-5-(dimethylamino)-1,3,4-thiadiazole | 1-(2-methylphenyl)piperidine | blue |
| 23 | 2-amino-5-(dimethylamino)-1,3,4-thiadiazole | 2-methyl-N,N-diethylaniline | blue |
| 24 | 2-amino-5-(dimethylamino)-1,3,4-thiadiazole | 2-methyl-N-(2-chloroethyl)-N-ethylaniline | blue |
| 25 | 2-amino-5-(dimethylamino)-1,3,4-thiadiazole | 2-methyl-N-ethyl-N-benzylaniline | blue |
| 26 | 2-amino-5-(dimethylamino)-1,3,4-thiadiazole | 2-methyl-N-ethyl-N-(2-phenoxyethyl)aniline | blue |

-continued

| # | Coupler | Developer | Color |
|---|---|---|---|
| 27 | 2-(dimethylamino)-5-amino-1,3,4-thiadiazole (N=N, CH3-N-CH3, S, C-NH2) | 2-fluoro-N,N-dimethylaniline | blue |
| 28 | 2-(dimethylamino)-5-amino-1,3,4-thiadiazole | 2-fluoro-N-ethyl-N-(2-acetoxyethyl)aniline (C2H5, C2H4O-C(=O)-CH3) | |
| 29 | 2-(dimethylamino)-5-amino-1,3,4-thiadiazole | 2-fluoro-N-ethyl-N-methylaniline (C2H5, CH3) | blue |
| 30 | 2-(dimethylamino)-5-amino-1,3,4-thiadiazole | 2-methoxy-N,N-dimethylaniline (OCH3, CH3, CH3) | blue |
| 31 | 2-(dimethylamino)-5-amino-1,3,4-thiadiazole | 1-aminonaphthalene (NH2) | blue |
| 32 | 2-(dimethylamino)-5-amino-1,3,4-thiadiazole | 1-(methylamino)naphthalene (N-CH3, H) | blue |
| 33 | 2-(dimethylamino)-5-amino-1,3,4-thiadiazole | 1-(ethylamino)naphthalene (N-C2H5, H) | blue |
| 34 | 2-(dimethylamino)-5-amino-1,3,4-thiadiazole | 1-(benzylamino)naphthalene (N-CH2-C6H5, H) | blue |
| 35 | 2-(dimethylamino)-5-amino-1,3,4-thiadiazole | 1-(dimethylamino)naphthalene (CH3, CH3) | blue |

-continued
| | | | |
|---|---|---|---|
| 36 | 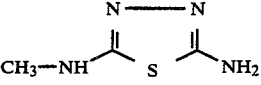 | 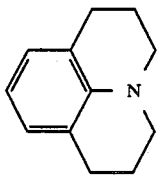 | blue |
| 37 | 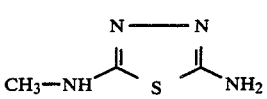 | 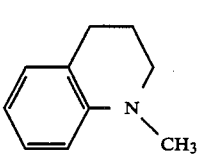 | blue |
| 38 | 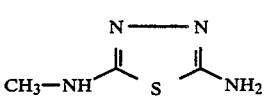 | 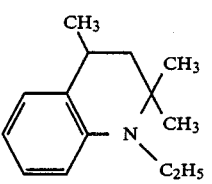 | blue |
| 39 | 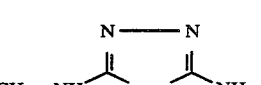 | 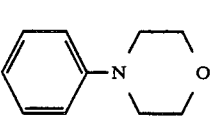 | blue |
| 40 | 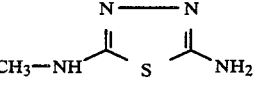 | 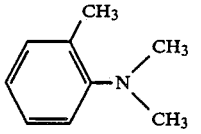 | blue |
| 41 | 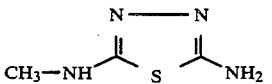 | 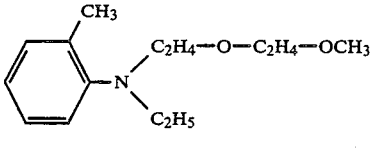 | blue |
| 42 | 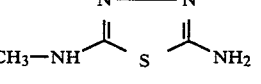 | 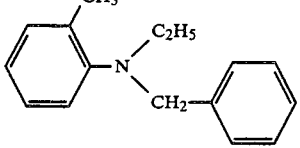 | blue |
| 43 | 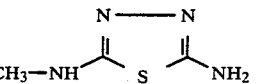 | 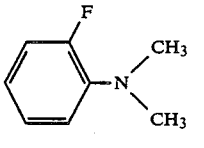 | blue |
| 44 | 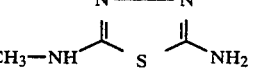 | 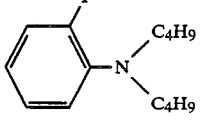 | blue |
| 45 | 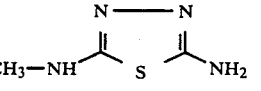 | 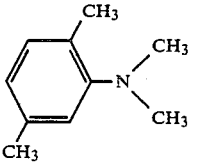 | blue |

-continued
| 46 | 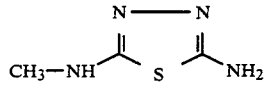 | 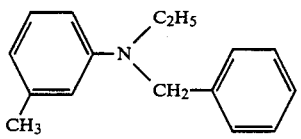 | blue |
| 47 | 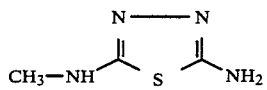 | 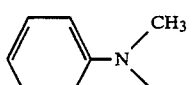 | blue |
| 48 | 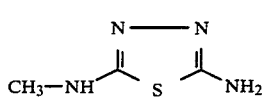 | 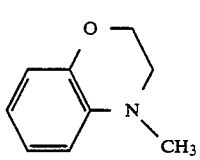 | blue |
| 49 | 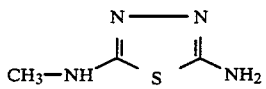 | 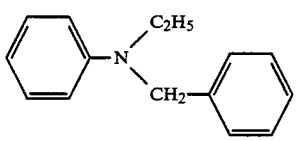 | blue |
| 50 | 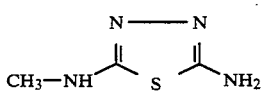 | 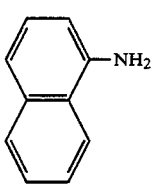 | blue |
| 51 | 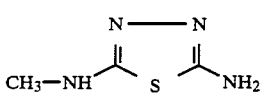 | 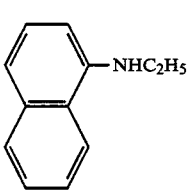 | blue |
| 52 | 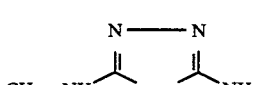 | 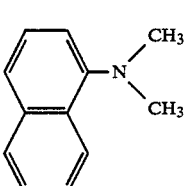 | blue |
| 53 | 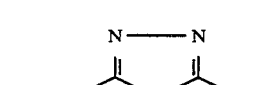 | 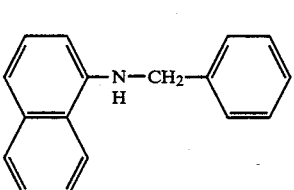 | blue |
| 54 | 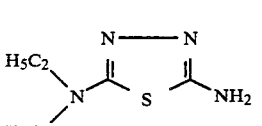 | 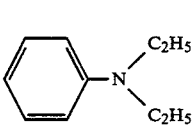 | blue |

-continued

| # | Diazo component | Coupling component | Color |
|---|---|---|---|
| 55 | (H5C2)2N-C(=NNH)-S-C(NH2)=N (diethylamino thiadiazole amine) | C6H5–N(C2H5)(C2H4OCOCH3) | blue |
| 56 | (H5C2)2N-C(=NNH)-S-C(NH2)=N | C6H5–N(C2H4O-CO-CH3)2 | blue |
| 57 | (H5C2)2N-C(=NNH)-S-C(NH2)=N | C6H5–N(C2H5)(C2H4–OCH3) | blue |
| 58 | (H5C2)2N-C(=NNH)-S-C(NH2)=N | C6H5–N(C2H5)(CH2C6H5) | blue |
| 59 | (H5C2)2N-C(=NNH)-S-C(NH2)=N | C6H5–N(C3H7)2 | blue |
| 60 | (H5C2)2N-C(=NNH)-S-C(NH2)=N | 2-(CH(CH3)CH2C(CH3)3)-C6H4–N(C2H5) | blue |
| 61 | (H5C2)2N-C(=NNH)-S-C(NH2)=N | C6H5–N(C4H9)2 | blue |
| 62 | (H5C2)2N-C(=NNH)-S-C(NH2)=N | 2-F-C6H4–N(CH3)2 | blue |
| 63 | (H5C2)2N-C(=NNH)-S-C(NH2)=N | 2-OCH3-C6H4–N(CH3)2 | blue |
| 64 | (H5C2)2N-C(=NNH)-S-C(NH2)=N | 3-CH3-C6H3–N(C3H7)(C2H7) | blue |

-continued

| # | Structure 1 | Structure 2 | Color |
|---|---|---|---|
| 65 | (H5C2)2N-C(S)-N=N-C(NH2) (thiadiazole) | 3-methyl-N-ethyl-N-benzylaniline | blue |
| 66 | (H5C2)2N-C(S)-N=N-C(NH2) (thiadiazole) | 2-fluoro-N,N-dimethylaniline | blue |
| 67 | (H5C2)2N-C(S)-N=N-C(NH2) (thiadiazole) | 1-(ethylamino)naphthalene | blue |
| 68 | (H5C2)2N-C(S)-N=N-C(NH2) (thiadiazole) | 1-naphthylamine | blue |
| 69 | (H5C2)2N-C(S)-N=N-C(NH2) (thiadiazole) | 1-(N,N-dimethylamino)naphthalene | blue |
| 70 | (iPr)2N-C(S)-N=N-C(NH2) (thiadiazole) | N-methyl-N-[2-(4-biphenylyloxy)ethyl]aniline | blue |
| 71 | (iPr)2N-C(S)-N=N-C(NH2) (thiadiazole) | N-butyl-N-[2-(benzoyloxy)ethyl]aniline | blue |
| 72 | (iPr)2N-C(S)-N=N-C(NH2) (thiadiazole) | julolidine | blue |
| 73 | (iPr)2N-C(S)-N=N-C(NH2) (thiadiazole) | 1-ethyl-2,2,4-trimethyl-1,2,3,4-tetrahydroquinoline | blue |

| | | | |
|---|---|---|---|
| 74 | 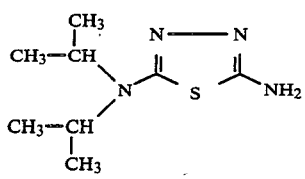 | 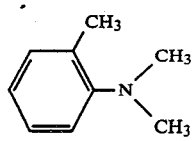 | blue |
| 75 | 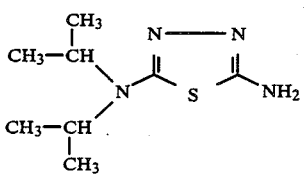 | 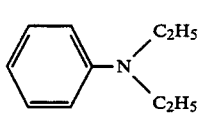 | blue |
| 76 | 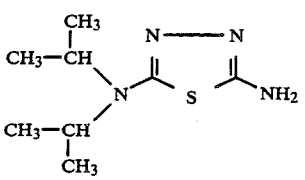 | 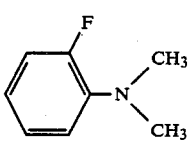 | blue |
| 77 | 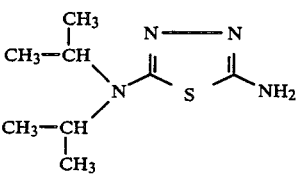 | 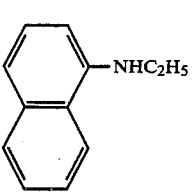 | |
| 78 | 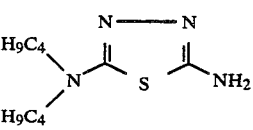 | 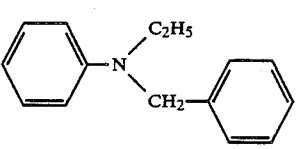 | blue |
| 79 | 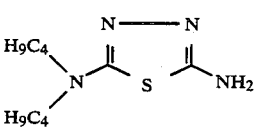 | 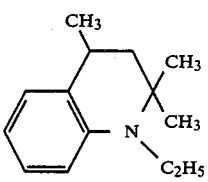 | blue |
| 80 | 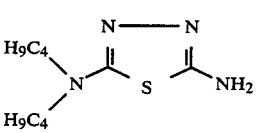 | 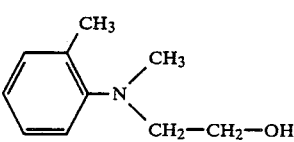 | blue |
| 81 | 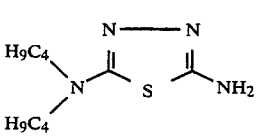 | 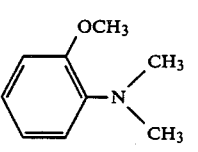 | blue |
| 82 | 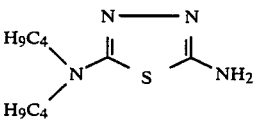 | 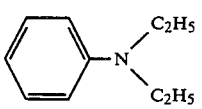 | blue |

-continued

| # | Structure 1 | Structure 2 | Color |
|---|---|---|---|
| 83 | H9C4\N–C(=S)–NH2 with N=N triazole, N(C4H9) | 1-naphthyl–NHC2H5 | blue |
| 84 | (H9C4–CH(C2H5)–CH2)2N–C(=S)–NH2 triazole | C6H5–N(C2H5)2 | blue |
| 85 | (H9C4–CH(C2H5)–CH2)2N–C(=S)–NH2 triazole | 2-methyl-6-(1-methyl-2-(1,1-dimethyl)ethyl)-N(C2H5)phenyl | blue |
| 86 | (H9C4–CH(C2H5)–CH2)2N–C(=S)–NH2 triazole | 2-OCH3–C6H4–N(C2H5)2 | blue |
| 87 | (H9C4–CH(C2H5)–CH2)2N–C(=S)–NH2 triazole | 1-naphthyl–NHC2H5 | blue |
| 88 | pyrrolidinyl–C(=S)–NH2 triazole | C6H5–N(CH3)2 | blue |
| 89 | pyrrolidinyl–C(=S)–NH2 triazole | C6H5–N(C2H4OCH3)(C2H5) | blue |
| 90 | pyrrolidinyl–C(=S)–NH2 triazole | 2-(1-methyl-2-(1,1-dimethyl)ethyl)-N(C2H5)phenyl | blue |
| 91 | pyrrolidinyl–C(=S)–NH2 triazole | 2-(2-methoxyethyl)-N(CH3)phenyl (morpholino-fused) | blue |

| 92 | 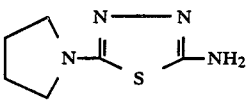 | 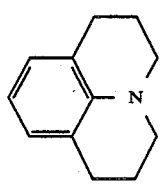 | blue |
| 93 | 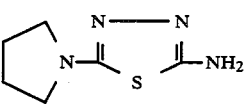 | 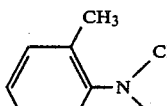 | blue |
| 94 | 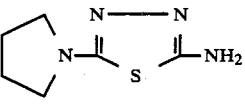 | 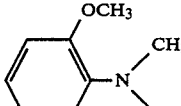 | blue |
| 95 | 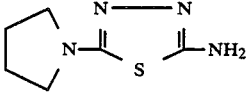 | 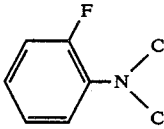 | blue |
| 96 | 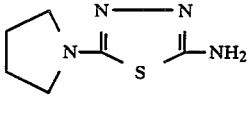 | 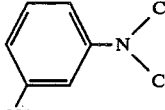 | blue |
| 97 | 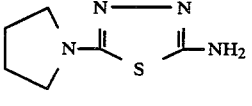 | 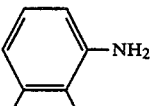 | blue |
| 98 | 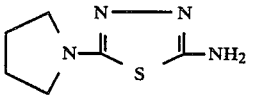 | 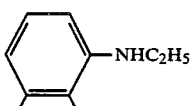 | blue |
| 99 | 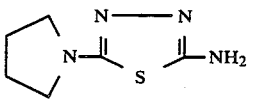 | 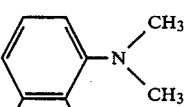 | blue |
| 100 | 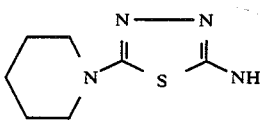 | 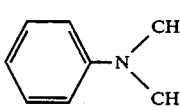 | blue |

| | | | |
|---|---|---|---|
| 101 | (piperidine-thiadiazole-C(S)-NH₂) | C₆H₅-N(C₂H₅)-CH₂CH₂-C₆H₅ | blue |
| 102 | (piperidine-thiadiazole-C(S)-NH₂) | C₆H₅-N(CH₃)-C₂H₄OCH₃ | blue |
| 103 | (piperidine-thiadiazole-C(S)-NH₂) | 2-methyl-N-pyrrolidinyl-benzene | blue |
| 104 | (piperidine-thiadiazole-C(S)-NH₂) | 2-methoxy-N,N-dimethylaniline | blue |
| 105 | (piperidine-thiadiazole-C(S)-NH₂) | 2-(N-methylamino)phenyl morpholine-like | blue |
| 106 | (piperidine-thiadiazole-C(S)-NH₂) | 2-(1,1,3-trimethylbutyl)-N-ethylaniline | blue |
| 107 | (piperidine-thiadiazole-C(S)-NH₂) | julolidine | blue |
| 108 | (piperidine-thiadiazole-C(S)-NH₂) | 1-(N-ethylamino)naphthalene | blue |
| 109 | (piperidine-thiadiazole-C(S)-NH₂) | 1-aminonaphthalene | blue |

-continued
| | | | |
|---|---|---|---|
| 110 | 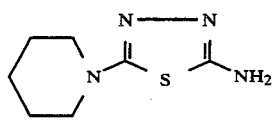 | 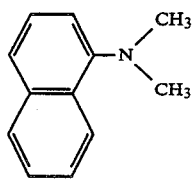 | blue |
| 111 | 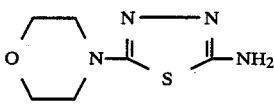 | 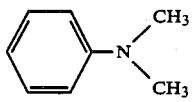 | blue |
| 112 | 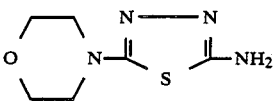 | 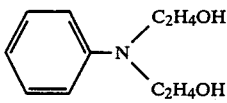 | blue |
| 113 | 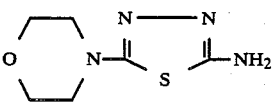 | 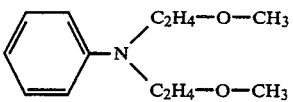 | blue |
| 114 | 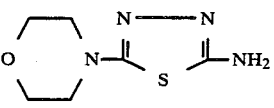 | 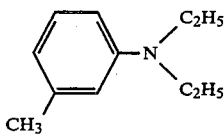 | blue |
| 115 | 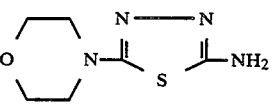 | 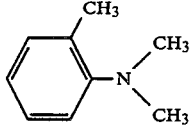 | blue |
| 116 | 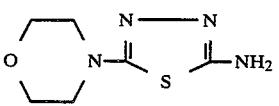 | 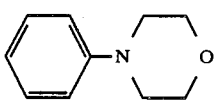 | blue |
| 117 | 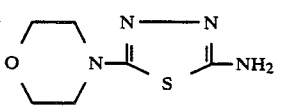 | 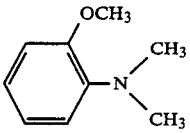 | blue |
| 118 | 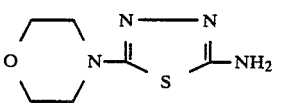 | 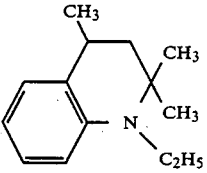 | blue |
| 119 | 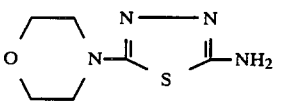 | 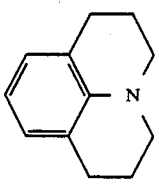 | blue |

-continued
| | | | |
|---|---|---|---|
| 120 | 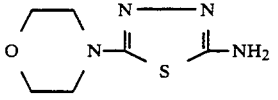 | 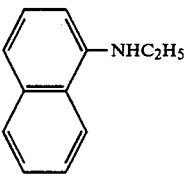 | blue |
| 121 | 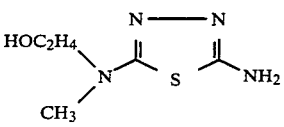 | 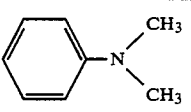 | blue |
| 122 | 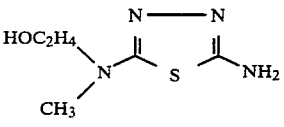 | 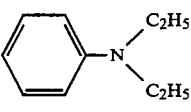 | blue |
| 123 | 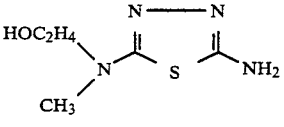 | 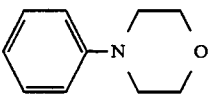 | blue |
| 124 | 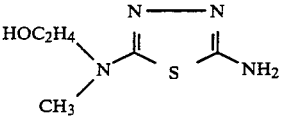 | 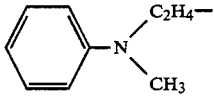 | blue |
| 125 | 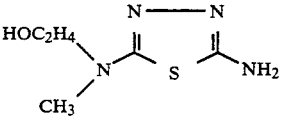 | 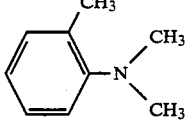 | blue |
| 126 | 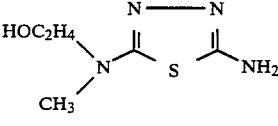 | 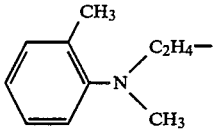 | blue |
| 127 | 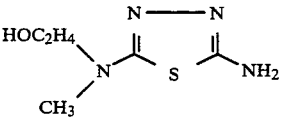 | 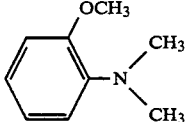 | blue |
| 128 | 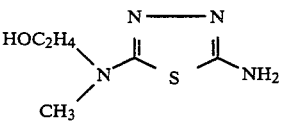 | 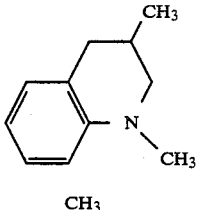 | blue |
| 129 | 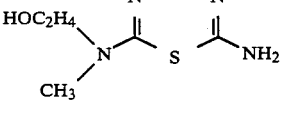 | 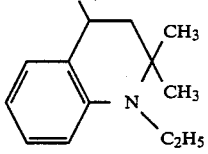 | blue |

-continued

| # | Structure 1 | Structure 2 | Color |
|---|---|---|---|
| 130 | HOC2H4\N(CH3)−C(=N−N=)−S−C(NH2)= | 2-(morpholinyl-like): phenyl with O−CH2CH2−N(CH3)− ortho | blue |
| 131 | HOC2H4\N(CH3)−C(=N−N=)−S−C(NH2)= | 2-F-C6H4−N(CH3)2 | blue |
| 132 | HOC2H4\N(CH3)−C(=N−N=)−S−C(NH2)= | 1-naphthyl−NH2 | blue |
| 133 | HOC2H4\N(CH3)−C(=N−N=)−S−C(NH2)= | 1-naphthyl−NHC2H5 | blue |
| 134 | HOC2H4\N(CH3)−C(=N−N=)−S−C(NH2)= | 1-naphthyl−N(CH3)2 | blue |
| 135 | HOC2H4\N(CH2C2OH)−C(=N−N=)−S−C(NH2)= | C6H5−N(C2H5)(CH2C6H5) | blue |
| 136 | HOC2H4\N(CH2C2OH)−C(=N−N=)−S−C(NH2)= | 2-CH3-C6H4−N(C2H5)(CH2C6H5) | blue |
| 137 | HOC2H4\N(CH2C2OH)−C(=N−N=)−S−C(NH2)= | 2-OCH3-C6H4−N(C2H5)(CH2C6H5) | blue |
| 138 | HOC2H4\N(CH2C2OH)−C(=N−N=)−S−C(NH2)= | 1,2,3,4-tetrahydroquinoline derivative with CH3, gem-di-CH3, N−C2H5 | blue |

-continued

| # | Structure 1 | Structure 2 | Color |
|---|---|---|---|
| 139 | (CH₃)CH(OH)-CH₂ and CH₃-CH(OH)-CH₂ groups on N of 1,3,4-thiadiazole-2-amine (5-position NH₂, with thione S) | C₆H₅-N(C₂H₅)₂ | blue |
| 140 | same diol-diisopropyl N-substituted thiadiazole-amine | C₆H₅-N(C₂H₅)(CH₂C₆H₅) | blue |
| 141 | same | 3-CH₃-C₆H₄-N(C₂H₅)(C₂H₄C₆H₅) | blue |
| 142 | same | 2-CH₃-C₆H₄-N(C₂H₅)(CH₂C₆H₅) | blue |
| 143 | same | 1,1,4-trimethyl-4-ethyl-1,2,3,4-tetrahydroquinoline | blue |
| 144 | same | 1-naphthyl-NHC₂H₅ | blue |
| 145 | same | 1-naphthyl-N(C₄H₉)₂ | blue |

4,500,715
-continued
| 146 | 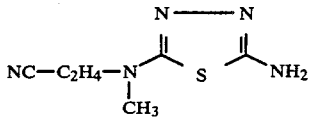 | 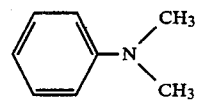 | blue |
| 147 | 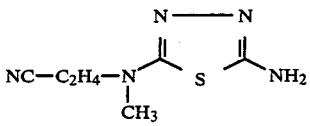 | 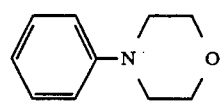 | blue |
| 148 | 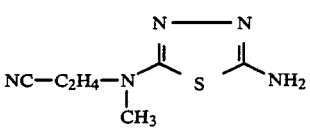 | 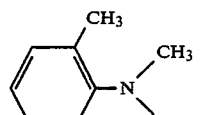 | blue |
| 149 | 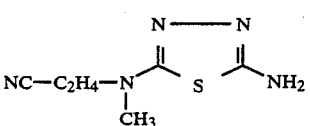 | 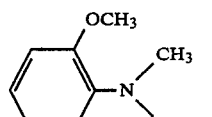 | blue |
| 150 | 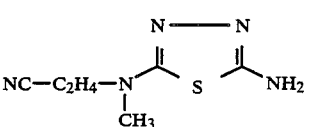 | 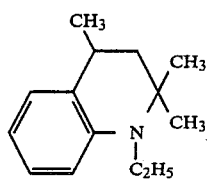 | blue |
| 151 | 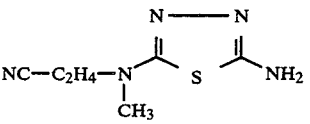 | 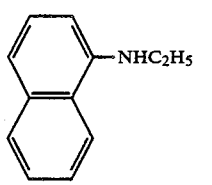 | blue |
| 152 | 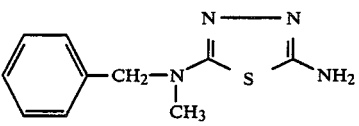 | 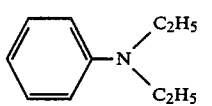 | blue |
| 153 | 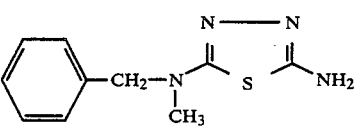 | 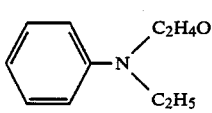 | blue |
| 154 | 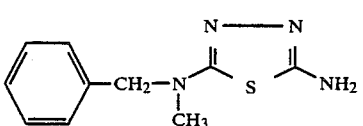 | 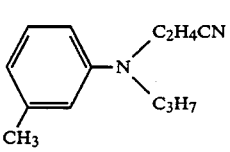 | blue |
| 155 | 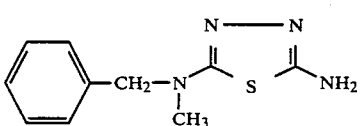 | 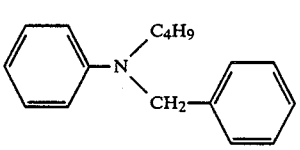 | blue |

-continued
| | | | |
|---|---|---|---|
| 156 | 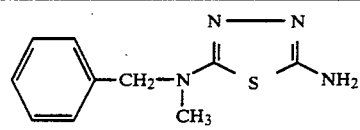 | 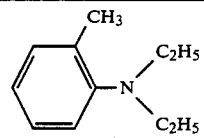 | blue |
| 157 | 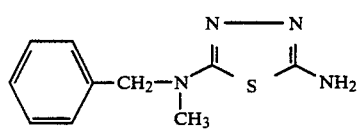 | 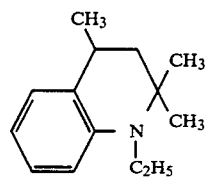 | blue |
| 158 | 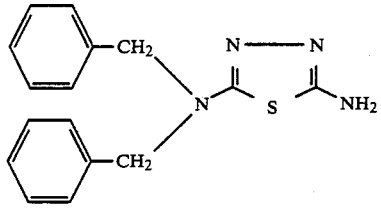 | 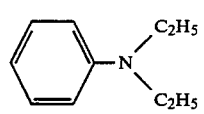 | blue |
| 159 | 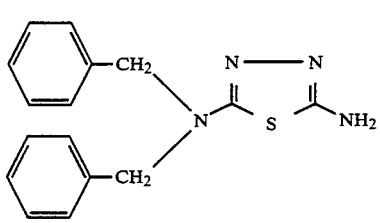 | 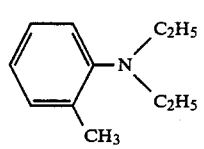 | blue |
| 160 | 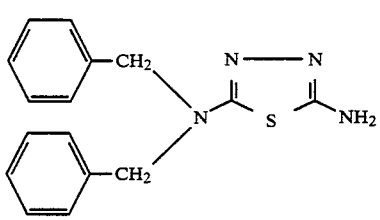 | 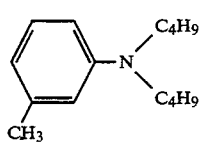 | blue |
| 161 | 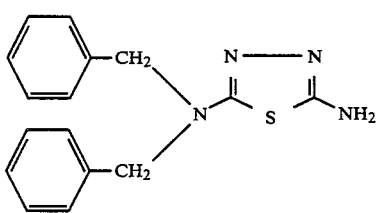 | 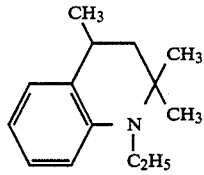 | blue |
| 162 | 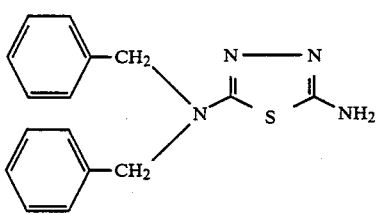 | 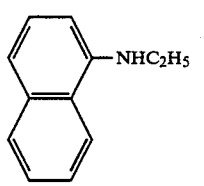 | blue |
| 163 | 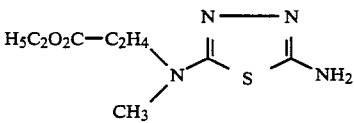 | 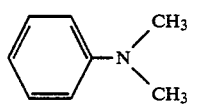 | blue |

| # | Structure 1 | Structure 2 | Color |
|---|---|---|---|
| 164 | H₅C₂O₂C—C₂H₄–N(CH₃)–C(S)–N=N–C(NH₂) (thiadiazole) | 2-CH₃-C₆H₄-N(CH₃)₂ | blue |
| 165 | H₅C₂O₂C—C₂H₄–N(CH₃)–C(S)–N=N–C(NH₂) (thiadiazole) | 2-(CH₃CH-CH₂-C(CH₃)₃)-C₆H₄-N(H)-C₂H₅ | blue |
| 166 | H₅C₂O₂C—C₂H₄–N(CH₃)–C(S)–N=N–C(NH₂) (thiadiazole) | 1-(NHC₂H₅)-naphthyl | blue |
| 167 | Cyclohexyl–N(CH₃)–C(S)–N=N–C(NH₂) (thiadiazole) | C₆H₅–N(C₂H₅)₂ | blue |
| 168 | Cyclohexyl–N(CH₃)–C(S)–N=N–C(NH₂) (thiadiazole) | 2-CH₃-C₆H₄-N(CH₃)₂ | blue |
| 169 | Cyclohexyl–N(CH₃)–C(S)–N=N–C(NH₂) (thiadiazole) | 3-CH₃-C₆H₄-N(C₂H₅)(CH₂C₆H₅) | blue |
| 170 | Cyclohexyl–N(CH₃)–C(S)–N=N–C(NH₂) (thiadiazole) | 1-(NH–CH₂–C₆H₅)-naphthyl | blue |
| 171 | CH₃–C(O)–N(CH₃)–C(S)–N=N–C(NH₂) (thiadiazole) | C₆H₅–N(C₂H₅)₂ | violet |
| 172 | CH₃–C(O)–N(CH₃)–C(S)–N=N–C(NH₂) (thiadiazole) | 2-CH₃-C₆H₄-N(CH₃)₂ | blue |

| | | | |
|---|---|---|---|
| 173 | 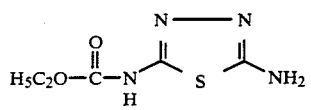 | 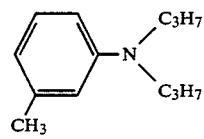 | violet |
| 174 | 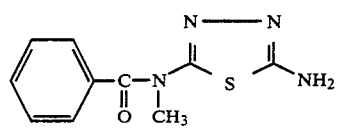 | 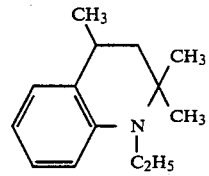 | blue |
| 175 | 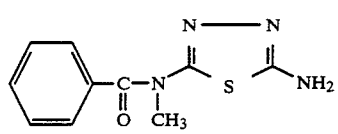 | 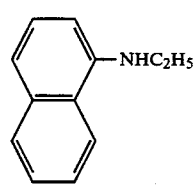 | blue |
| 176 | 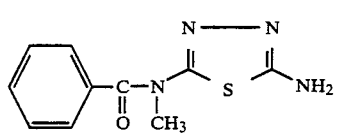 | 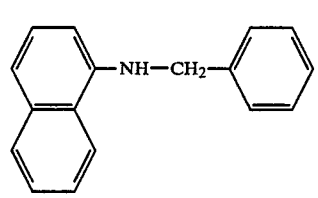 | blue |
| 177 | 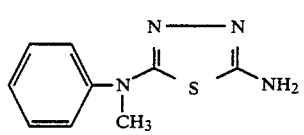 | 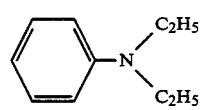 | blue |
| 178 | 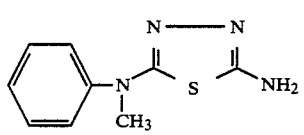 | 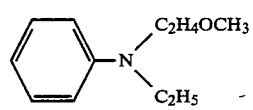 | blue |
| 179 | 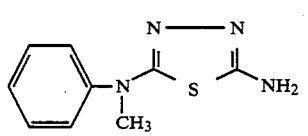 | 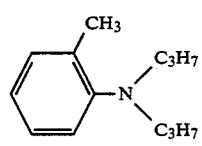 | blue |
| 180 | 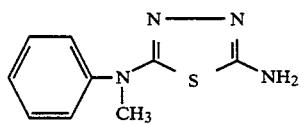 | 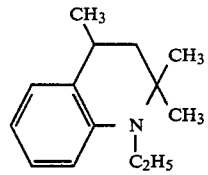 | blue |
| 181 | 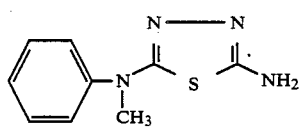 | 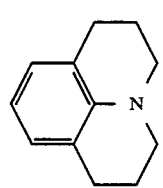 | blue |

| # | Structure 1 | Structure 2 | Color |
|---|---|---|---|
| 182 | Ph-N(CH₃)-C(=S)-N=N-C(NH₂)= | 2-OCH₃-C₆H₄-N(C₂H₅)₂ | blue |
| 183 | Ph-N(CH₃)-C(=S)-N=N-C(NH₂)= | 1-naphthyl-NHC₂H₅ | blue |
| 184 | H₅C₂-NH-C(=O)-NH-C(=S)-N=N-C(NH₂)= | C₆H₅-N(C₂H₅)₂ | violet |
| 185 | H₅C₂-NH-C(=O)-NH-C(=S)-N=N-C(NH₂)= | 3-CH₃-C₆H₄-N(C₄H₉)₂ | violet |
| 186 | H₅C₂-NH-C(=O)-NH-C(=S)-N=N-C(NH₂)= | 2-CH₃-C₆H₄-N(CH₃)₂ | violet |
| 187 | H₅C₂-NH-C(=O)-NH-C(=S)-N=N-C(NH₂)= | 1-naphthyl-NH-CH₂-C₆H₅ | violet |
| 188 | C₂H₅-SO₂-NH-C(=S)-N=N-C(NH₂)= | C₆H₅-N(C₄H₉)₂ | violet |
| 189 | C₂H₅-SO₂-NH-C(=S)-N=N-C(NH₂)= | 2-CH₃-C₆H₄-N(CH₃)₂ | violet |
| 190 | (CH₃)₂N-SO₂-NH-C(=S)-N=N-C(NH₂)= | 3-CH₃-C₆H₄-N(C₄H₉)(C₂H₄-O-C₆H₅) | violet |
| 191 | 4-CH₃O-C₆H₄-N(CH₃)-C(=S)-N=N-C(NH₂)= | C₆H₅-N(C₂H₄-OC₂H₅)(C₂H₅) | blue |

-continued

| | | | |
|---|---|---|---|
| 192 | 4-methoxyphenyl-N(CH₃)-C(=S)-N=N-C(S)-NH₂ (1,2,4-thiadiazole with 4-MeO-C₆H₄, N-CH₃) | 2-CH₃-C₆H₄-N(pyrrolidine) | blue |
| 193 | 4-methoxyphenyl-N(CH₃)-(1,2,4-thiadiazol-3-yl)-5-NH₂ | 2-CH₃-C₆H₄-N(C₂H₅)(CH₂CH(CH₃)C(CH₃)₃) | blue |
| 194 | (CH₃)₃C-NH-(1,2,4-thiadiazol-3-yl)-5-NH₂ | C₆H₅-N(CH₃)₂ | blue |
| 195 | (CH₃)₃C-NH-(1,2,4-thiadiazol-3-yl)-5-NH₂ | C₆H₅-N(CH₃)(C₂H₄OH) | blue |
| 196 | (CH₃)₃C-NH-(1,2,4-thiadiazol-3-yl)-5-NH₂ | C₆H₅-N(C₂H₅)(C₂H₄-OCH₃) | blue |
| 197 | (CH₃)₃C-NH-(1,2,4-thiadiazol-3-yl)-5-NH₂ | 2-CH₃-C₆H₄-N(C₄H₉)₂ | blue |
| 198 | (CH₃)₃C-NH-(1,2,4-thiadiazol-3-yl)-5-NH₂ | 2-[N(CH₃)]-C₆H₄-CH₂CH(CH₃)CH₂- (tetrahydroquinoline derivative) | blue |
| 199 | (CH₃)₃C-NH-(1,2,4-thiadiazol-3-yl)-5-NH₂ | julolidine (1,2,3,4-tetrahydroquinoline fused) | blue |
| 200 | (CH₃)₃C-NH-(1,2,4-thiadiazol-3-yl)-5-NH₂ | 2-OCH₃-C₆H₄-N(CH₃)₂ | blue |
| 201 | (CH₃)₃C-NH-(1,2,4-thiadiazol-3-yl)-5-NH₂ | 1-(NHC₂H₅)-naphthyl | blue |

-continued

| # | Structure 1 | Structure 2 | Color |
|---|---|---|---|
| 202 | CH₃—(CH₂)₃—CH(C₂H₅)—CH₂—NH—C(S)—N=N—C(NH₂) | C₆H₄—N(C₂H₅)₂ | blue |
| 203 | CH₃—(CH₂)₃—CH(C₂H₅)—CH₂—NH—C(S)—N=N—C(NH₂) | 2-CH₃-C₆H₄—N(CH₂—CH=CH₂)₂ | blue |
| 204 | CH₃—(CH₂)₃—CH(C₂H₅)—CH₂—NH—C(S)—N=N—C(NH₂) | 3,5-(CH₃)-C₆H₃—N(C₂H₅)(C₄H₉) | blue |
| 205 | CH₃—(CH₂)₃—CH(C₂H₅)—CH₂—NH—C(S)—N=N—C(NH₂) | 1-naphthyl—NH—CH₂—C₆H₅ | blue |
| 206 | CH₂=CH—CH₂—NH—C(S)—N=N—C(NH₂) | C₆H₅—N(C₃H₇)₂ | blue |
| 207 | CH₂=CH—CH₂—NH—C(S)—N=N—C(NH₂) | 2-CH₃-C₆H₄—N(CH₃)₂ | blue |
| 208 | CH₂=CH—CH₂—NH—C(S)—N=N—C(NH₂) | 3-CH₃-C₆H₄—N(C₄H₉)₂ | blue |
| 209 | CH₂=CH—CH₂—NH—C(S)—N=N—C(NH₂) | 2-(O—)C₆H₄—N(CH₃) (morpholine-type) | blue |
| 210 | (CH₂=CH—CH₂)₂N—C(S)—N=N—C(NH₂) | C₆H₅—N(CH₃)(C₂H₄—OCH₃) | blue |
| 211 | (CH₂=CH—CH₂)₂N—C(S)—N=N—C(NH₂) | 2-CH₃-C₆H₄—N(piperidinyl) | blue |

| No. | Structure 1 | Structure 2 | Color |
|---|---|---|---|
| 212 | (CH₂=CH—CH₂)₂N—C(S)—N=N—C(NH₂) (1,3,4-thiadiazole with diallylamino and amino) | 3-methyl-N-methyl-N-benzylaniline | blue |
| 213 | (CH₂=CH—CH₂)₂N—C(S)—N=N—C(NH₂) (1,3,4-thiadiazole with diallylamino and amino) | 2-(1,3,3-trimethylbutyl)-N-ethylaniline | blue |
| 214 | H₂N—C(S)—N=N—C(NH₂) (2,5-diamino-1,3,4-thiadiazole) | N,N-dimethylaniline | violet |
| 215 | H₂N—C(S)—N=N—C(NH₂) (2,5-diamino-1,3,4-thiadiazole) | 2-methyl-N,N-dimethylaniline | blue |
| 216 | H₂N—C(S)—N=N—C(NH₂) (2,5-diamino-1,3,4-thiadiazole) | 3-methyl-N,N-diethylaniline | voilet |
| 217 | H₂N—C(S)—N=N—C(NH₂) (2,5-diamino-1,3,4-thiadiazole) | julolidine | blue |
| 218 | CH₃—O—C₂H₄—N(CH₃)—C(S)—N=N—C(NH₂) | N,N-dimethylaniline | blue |
| 219 | CH₃—O—C₂H₄—N(CH₃)—C(S)—N=N—C(NH₂) | 2-methyl-N,N-dimethylaniline | blue |
| 220 | CH₃—O—C₂H₄—N(CH₃)—C(S)—N=N—C(NH₂) | N-methyl-1,2,3,4-tetrahydroquinoline | blue |
| 221 | CH₃—O—C₂H₄—N(CH₃)—C(S)—N=N—C(NH₂) | 2-(1,3,3-trimethylbutyl)-N-methylaniline | blue |

-continued
| 222 | 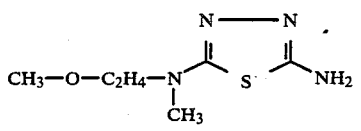 | 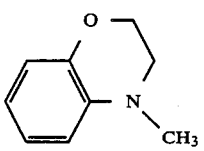 | blue |
| 222 | 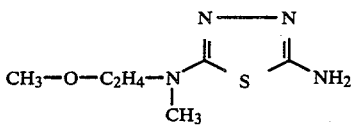 | 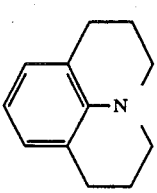 | blue |
| 224 | 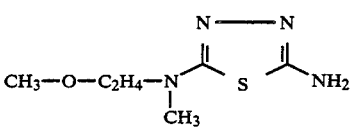 | 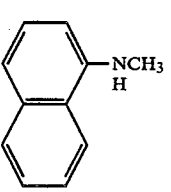 | blue |
| 225 | 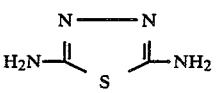 | 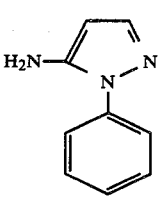 | orange |
| 226 | 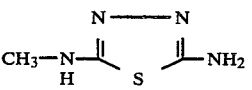 | 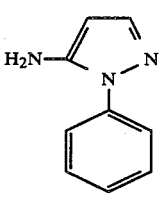 | orange |
| 227 | 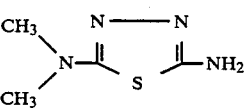 | 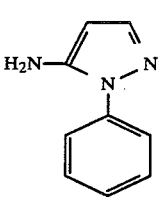 | scarlet |
| 228 | 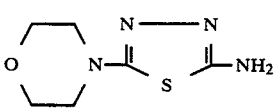 | 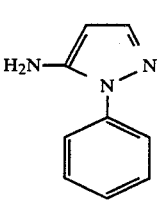 | scarlet |
| 229 | 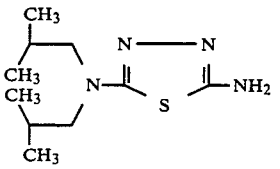 | 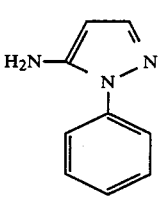 | scarlet |

| | | | |
|---|---|---|---|
| 230 | H₂N-C(=N-N=)-S-C(=NH)-NH₂ (1,2,4-thiadiazole-3,5-diamine) | 3-methyl-5-amino-1-phenylpyrazole | orange |
| 231 | CH₃NH-C(=N-N=)-S-C(=NH)-NH₂ | 3-methyl-5-amino-1-phenylpyrazole | orange |
| 232 | (CH₃)₂N-C(=N-N=)-S-C(=NH)-NH₂ | 3-methyl-5-amino-1-phenylpyrazole | orange |
| 233 | H₂N-C(=N-N=)-S-C(=NH)-NH₂ | 3-methyl-5-amino-1-methylpyrazole | orange |
| 234 | CH₃NH-C(=N-N=)-S-C(=NH)-NH₂ | 3-methyl-5-amino-1-methylpyrazole | orange |
| 235 | (CH₃)₂N-C(=N-N=)-S-C(=NH)-NH₂ | 3-methyl-5-amino-1-methylpyrazole | orange |
| 236 | H₂N-C(=N-N=)-S-C(=NH)-NH₂ | 5-amino-1-methylpyrazole | orange |
| 237 | CH₃NH-C(=N-N=)-S-C(=NH)-NH₂ | 5-amino-1-methylpyrazole | orange |
| 238 | (CH₃)₂N-C(=N-N=)-S-C(=NH)-NH₂ | 5-amino-1-methylpyrazole | orange |

-continued

| Example | Diazo component | Coupling component | | Colour shade |
|---|---|---|---|---|
| 239 | H₂N–C(=N–N=)–S–C(=NH)–NH₂ (1,2,4-thiadiazole-3,5-diamine) | 3-methyl-5-amino-1H-pyrazole | | orange |
| 240 | CH₃–NH–C(=N–N=)–S–C(=NH)–NH₂ | 3-methyl-5-amino-1H-pyrazole | | orange |
| 241 | (CH₃)₂N–C(=N–N=)–S–C(=NH)–NH₂ | 3-methyl-5-amino-1H-pyrazole | | orange |
| 242 | H₂N–C(=N–N=)–S–C(=NH)–NH₂ | 5-amino-1H-pyrazole | | orange |
| 243 | CH₃–NH–C(=N–N=)–S–C(=NH)–NH₂ | 5-amino-1H-pyrazole | | orange |
| 244 | (CH₃)₂N–C(=N–N=)–S–C(=NH)–NH₂ | 5-amino-1H-pyrazole | | orange |

If the procedure followed is as described in Example 1 and the diazo components and coupling components listed in the table which follows and the quaternising agents are used, corresponding dyestuffs which dye polyacrylonitrile in the colour shades indicated, with similar fastness properties, are obtained.

| Example | Diazo component | Coupling component | Quaternising agent | Colour shade |
|---|---|---|---|---|
| 245 | CH₃–NH–C(=N–N=)–S–C(=NH)–NH₂ | 2-ethyl-N,N-dimethylaniline | $CH_3Cl$ | blue |
| 246 | " | 8-methyl-1,1,3-trimethyl-N-methyl-tetrahydroquinoline derivative | benzyl chloride ($C_6H_5$–$CH_2Cl$) | " |
| 247 | " | 8-methyl-julolidine | $CH_3$–C₆H₄–$SO_2$–$OCH_3$ | " |
| 248 | " | 2-methoxy-N,N-diethylaniline | $(C_2H_5O)_2$–$SO_2$ | " |

-continued

| Example | Diazo component | Coupling component | Quaternising agent | Colour shade |
|---|---|---|---|---|
| 249 | (CH3)2N-C(S)-N=N-C(NH2) | 2-CH3, N(CH3)2 aniline | CH₃Br | " |
| 250 | " | N,N-bis(allyl)aniline | C₂H₅Cl | " |
| 251 | " | 2-methylindole (NH) | C₆H₅—SO₂—OC₂H₅ | red |
| 252 | " | 2-phenyl-1-methylindole | CH₂=CH—CO NH₂ | ruby |
| 253 | " | 3-methyl-N,N-dibenzylaniline | CH₂=CH—CH₂—Br | blue |
| 254 | (CH3)2C(CH2)2N(H)-C(S)-N=N-C(NH2) | N,N-dibenzylaniline | (C₂H₅O)₂SO₂ | " |
| 255 | " | 3-methyl-N-butyl-N-(2-phenoxyethyl)aniline | epoxide (CH₂—O—CH₂) | " |
| 256 | " | 2-methylindole (NH) | C₂H₅Br | red |
| 257 | CH₃—(CH₂)₃—CH(C₂H₅)—CH₂ group, bis, N—C(S)—N=N—C(NH₂) | 3-CH3, N(C₂H₄CN)(C₂H₅) aniline | CH₃—C₆H₄—SO₂—OCH₃ | blue |
| 258 | " | 8-methyl-julolidine | CH₂=CH—CH₂Cl | blue |

| Example | Diazo component | Coupling component | Quaternising agent | Colour shade |
|---|---|---|---|---|
| 259 | " | 2-phenyl-1-methyl-indole | phenyl-CH₂Cl | ruby |
| 260 | N-phenyl-N-methyl-N'-(thiocarbamoyl)-amidrazone (with N=N, S, NH₂) | N,N-diethylaniline | CH₃-C₆H₄-SO₂-OC₂H₅ | blue |
| 261 | " | N-benzyl-N-methyl-m-toluidine | ethylene oxide (CH₂-O-CH₂) | " |
| 262 | " | 2-methylindole | phenyl-CH₂-Br | red |
| 263 | " | N,N,2,2,4-pentamethyl-...-aniline derivative | C₂H₅Cl | blue |
| 264 | N-(4-chloro-2-methylphenyl)-N-methyl amidrazone-thiocarbamoyl | 2-phenyl-1-methyl-indole | CH₂=CH-CH₂Br | ruby |
| 265 | " | 1-(2-methylphenyl)pyrrolidine | (C₂H₅O)₂SO₂ | blue |
| 266 | " | N-(2-phenylethyl)-N-(2-cyanoethyl)-m-toluidine | CH₂=CH-CONH₂ | " |
| 267 | N-cyclohexyl-N-methyl amidrazone-thiocarbamoyl | N,N-dimethylaniline | CH₃Br | " |
| 268 | " | 2-fluoro-N,N-diethylaniline | C₂H₅Br | " |

EXAMPLE 269

6 parts of dimethyl sulphate are added in portions to 5 parts of dyestuff bases, prepared as in Example 1, of the formula

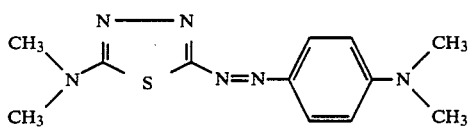

in 100 parts of chlorobenzene at 100°–110° C. The mixture is then heated to the boiling point for 30 minutes. After cooling, the dyestuff is filtered off, washed with benzene and dried. 5.8 parts of a powder of the formula

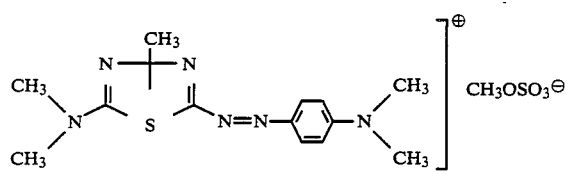

which readily dissolves in water to give a blue-coloured solution and dyes textile materials made of polyacrylonitrile in blue shades with very good fastness to light and wet processing, are obtained.

The dyestuffs described in Examples 2 to 248 can be obtained as the methosulphates in an analogous manner.

EXAMPLE 270

Dyeing process for polyacrylonitrile and acid-modified polyamide fibres (of the Dye I type):

0.1 part of the dyestuff prepared according to Example 1 is made into a paste with about 2 parts of water, a little acetic acid being added if necessary, and the paste is dissolved in 50 parts of hot water. 0.5–2 g of a condensation product of naphthalenesulphonic acid and formaldehyde are also added to the dye liquor and the liquor is made up to 500 parts with cold water. The pH value of the dye liquor is adjusted to 4.5–5 with acetic acid or sodium acetate. 10 g of piece goods of polyacrylonitrile fibres or acid-modified polyamide fibres are kept in continuous motion in this dye liquor, whilst the temperature is increased to 100° C. in the course of 30 minutes. Dyeing is carried out at the boiling point for 60 minutes and the material is rinsed with cold water and then dried at 60°–70° C. For dyeing acid-modified polyglycol terephthalate fibres (of the Dacron 64 type), a carrier, for example 1–3 parts of an aromatic hydroxycarboxylic acid ester or diphenyl, is also added to the dye liquor.

Printing process:

A woven polyacrylonitrile fabric is printed with a printing paste which has been prepared in the following manner: 330 parts by weight of hot water are poured over 30 parts by weight of the dyestuff of the formula in Example 1, 50 parts by weight of diethylene thioglycol, 30 parts by weight of cyclohexanol and 30 parts by weight of 30% strength acetic acid and the resulting solution is added to 500 parts by weight of crystal gum (gum arabic as a thickener). Finally, 30 parts by weight of zinc nitrate solution are also added. The resulting print is dried, steamed for 30 minutes and then rinsed. A blue print of very good fastness properties is obtained.

PREPARATION EXAMPLES FOR COMPOUNDS OF THE FORMULA (VII)

Example a 36 parts of 2-amino-5-bromo-1,3,4-thiadiazole are made into a slurry with 100 parts of ethanol, and 75 parts of 50% strength dimethylamine solution are added. The reaction mixture is stirred at the boiling point for 2 hours. After cooling, the almost colourless crystals are filtered off, washed with cold water and dried at 50° C. in vacuo.

Melting point: 225°–226°

Example b 36 parts of 2-amino-5-bromo-1,3,4-thiadiazole are suspended in 200 parts of ethanol, and 45 parts of dipropylamine are added. The reaction mixture is boiled under reflux for 2 hours and then concentrated to dryness. The residue is made into a slurry with 250 ml of water and the resulting crystal sludge is filtered. The 5-dipropylamino-2-amino-1,3,4-thiadiazole thus prepared can be recrystallised from ethanol/water.

Melting point: 152°–153°

The same product is obtained if, instead of 2-amino-5-bromo-1,3,4-thiadiazole, the following compounds are employed: 2-amino-5-chloro-1,3,4-thiadiazole, 2-amino-5-methylsulphonyl-1,3,4-thiadiazole and 2-amino-5-ethylsulphonyl-1,3,4-thiadiazole.

Example c 28 parts of dibutylamine and 25 parts of triethylamine are added to 27 parts of 2-amino-5-chloro-1,3,4-thiadiazole in 200 parts of ethanol. The reaction mixture is heated under reflux for 2 hours and then concentrated to dryness. The residue is suspended in 250 ml of water and filtered. The 2-amino-5-dibutylamino-1,3,4-thiadiazole obtained in this manner can be recrystallised from ethanol/water.

Melting point: 116°–117°

The same product is obtained if, instead of 2-amino-5-chloro-1,3,4-thiadiazole, the following compounds are employed: 2-amino-5-bromo-1,3,4-thiadiazole, 2-amino-5-methylsulphonyl-1,3,4-thiadiazole and 2-amino-5-ethylsulphonyl-1,3,4-thiadiazole.

Instead of 25 parts of triethylamine, equivalent amounts of pyridine, pyrimidine and other tertiary nitrogen bases customary in organic chemistry can be employed with the same result.

Example d 39 parts of 2-amino-5-ethylsulphonyl-1,3,4-thiadiazole in 200 parts of dimethylformamide are warmed to 100° with 23 parts of N-methylcyclohexylamine and 20 parts of pyridine for 2 hours. Thereafter, the reaction mixture is concentrated to dryness and the residue is suspended in 250 ml of water and filtered off. 2-Amino-5-(N-methyl-N-cyclohexyl)amine can be recrystallized from ethanol/water.

Melting point: 168°–169°

Example e 36 parts of 2-amino-5-methylsulphonyl-1,3,4-thiadiazole in 100 parts of diisopropylamine are heated under reflux for 30 minutes. Excess diisopropylamine is distilled off and the residue is extracted with water. The 2-amino-5-diisopropylamino-1,3,4-thiadiazole which remains can be recrystallised from alcohol/water.

Melting point: 182°–183°

The following compounds can be prepared by processes analogous to those described in Examples a-e: 2-amino-5-diethylamino-1,3,4-thiadiazole, 2-amino-5-(N-methyl-N-ethyl)-amino-1,3,4-thiadiazole, 2-amino-5-diisobutylamino-1,3,4-thiadiazole, 2-amino-5-(N-ethyl-N-butyl)-amino-1,3,4-thiadiazole, 2-amino-5-(N-ethyl-N-propyl)-amino-1,3,4-thiadiazole, 2-amino-5-di(2-ethylhexyl)-amino-1,3,4-thiadiazole, 2-amino-5-(N-methyl-N-octadecyl)-amino-1,3,4-thiadiazole, 2-amino-5-dibenzylamino-1,3,4-thiadiazole, 2-amino-5-(N-methyl-N-benzyl)-amino-1,3,4-thiadiazole, 2-amino-5-diallylamino-1,3,4-thiadiazole, 2-amino-5-(1-methylhydrazino)-1,3,4-thiadiazole, 2-amino-5-(N-methyl-N-cyanoethyl)-amino-1,3,4-thiadiazole, 2-amino-5-di(2-cyanoethyl)-amino-1,3,4-thiadiazole, 2-amino-5-dimethallylamino-1,3,4-thiadiazole, 2-amino-5-piperidino-1,3,4-thiadiazole, 2-amino-5-pyrrolidino-1,3,4-thiadiazole, 2-amino-5-morpholino-1,3,4-thiadiazole and 2-amino-5-(N'-methyl)-piperazino-1,3,4-thiadiazole.

I claim:

1. Thiadiazole derivatives of the general formula

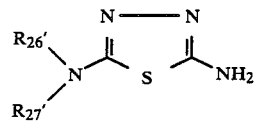

wherein
$R_{26}'$ denotes a $C_1$–$C_8$-alkyl radical which is optionally substituted by hydroxyl, halogen, cyano, $C_1$–$C_4$-alkoxy, carboxyl, aminocarbonyl or $C_1$–$C_4$-alkoxycarbonyl, a $C_2$–$C_4$-alkenyl radical, a cyclohexyl radical which is optionally substituted by $C_1$–$C_4$-alkyl, a phenyl, benzyl or phenylethyl radical which is optionally substituted by halogen, $C_1$–$C_4$-alkyl or $C_1$–$C_4$-alkoxy, a $C_1$–$C_2$-alkylcarbonyl, $C_1$–$C_4$-alkoxycarbonyl, mono- or di-$C_1$–$C_4$-alkylaminocarbonyl, aminocarbonyl, mono- or di-$C_1$–$C_4$-alkylaminosulphonyl, 2-thienyl, 2-furyl, 2-tetrahydrofuryl, amino, $C_1$–$C_4$-alkylamino or di-($C_1$–$C_4$-alkyl)-amino radical or a phenylamino or benzylamino radical which is optionally substituted by $C_1$–$C_4$-alkyl or $C_1$–$C_4$-alkoxy and $R_{27}'$ denotes a $C_1$–$C_8$-alkyl radical which is optionally substituted by hydroxyl, halogen, cyano, $C_1$–$C_4$-alkoxy, carboxyl, aminocarbonyl- or $C_1$–$C_4$-alkoxycarbonyl, a $C_2$–$C_4$-alkenyl radical or a benzyl or phenylethyl radical which is substituted by halogen, $C_1$–$C_4$-alkyl or $C_1$–$C_4$-alkoxy.

* * * * *